US007842823B2

(12) United States Patent
Chang

(10) Patent No.: US 7,842,823 B2
(45) Date of Patent: Nov. 30, 2010

(54) FLUOROGENIC PROBES FOR REACTIVE OXYGEN SPECIES

(75) Inventor: Christopher J. Chang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 806 days.

(21) Appl. No.: 11/588,785

(22) Filed: Oct. 27, 2006

(65) Prior Publication Data

US 2007/0141658 A1 Jun. 21, 2007

Related U.S. Application Data

(60) Provisional application No. 60/731,085, filed on Oct. 27, 2005.

(51) Int. Cl.
*C07D 311/80* (2006.01)
*C07F 7/08* (2006.01)
*G01N 33/50* (2006.01)

(52) U.S. Cl. .............................. 549/213; 544/69; 436/68
(58) Field of Classification Search ................. 549/213; 544/69; 436/68
See application file for complete search history.

(56) References Cited

U.S. PATENT DOCUMENTS

| | | | |
|---|---|---|---|
| 3,654,090 | A | 4/1972 | Wilhelmus et al. |
| 3,850,752 | A | 11/1974 | Schuurs et al. |
| 3,996,345 | A | 12/1976 | Ullman et al. |
| 4,351,760 | A | 9/1982 | Khanna et al. |
| 4,391,904 | A | 7/1983 | Litman et al. |
| 4,711,955 | A | 12/1987 | Ward et al. |
| 4,739,044 | A | 4/1988 | Stabinsky |
| 4,757,141 | A | 7/1988 | Fung et al. |
| 5,047,519 | A | 9/1991 | Hobbs, Jr. et al. |
| 5,049,673 | A | 9/1991 | Tsien et al. |
| 5,143,854 | A | 9/1992 | Pirrung et al. |
| 5,362,628 | A | 11/1994 | Haugland et al. |
| 5,453,517 | A | 9/1995 | Kuhn et al. |
| 5,459,268 | A | 10/1995 | Haugland et al. |
| 5,504,975 | A | 4/1996 | Bar et al. |
| 5,576,424 | A | 11/1996 | Mao et al. |
| 5,648,270 | A | 7/1997 | Kuhn et al. |
| 5,686,261 | A | 11/1997 | Zhang et al. |
| 6,638,644 | B2 * | 10/2003 | Zheng et al. .............. 428/690 |
| 2005/0186555 | A1 | 8/2005 | Lippard et al. |
| 2005/0214807 | A1 | 9/2005 | Johnson et al. |

OTHER PUBLICATIONS

Chang et al. (Journal of the American Chemical Society (2004), 126(47), 15392-15393).*
Agrawal et al., "Site-specific functionalization of oligodeoxynucleotides for non-radioactive labelling", *Tetrahedron Letters*, vol. 31, pp. 1543-1546 (1990).
Akasaka et al., "Study on aromatic phosphines for novel fluorometry of hydroperoxides (I)—synthesis and spectral properties of diphenyl aryl phosphines and their oxides", *Anal. Lett.*, vol. 20, pp. 731-745 (1987).
Avshalumov et al., "Endogenous hydrogen peroxide regulates the excitability of midbrain dopamine neurons via ATP-sensitive, potassium channels", *J. Neurosci.*, vol. 25, pp. 4222-4231 (2005).
Avshalumov et al, "Activation of ATP-sensitive K+ (KATP) channels by H2O2 underlies glutamate-dependent inhibition of striatal dopamine release", *Proc. Nat. Acad. Sci.*, vol. 100, pp. 11729-11734, (2003).
Balaban et al., "Mitochondria, oxidants, and aging", *Cell*, vol. 2005, pp. 483-495 (2005).
Baldwin et al., "Cloning and expression of the *luxY* gene from *Vibrio fischeri* strain Y-1 in *Escherichia coli* and complete amino acid sequence of the yellow fluorescent protein", *Biochemistry*, vol. 29, pp. 5509-5515 (1990).
Barnham et al., "Neurodegenerative diseases and oxidative stress", *Nat. Rev. Drug Discovery*, vol. 3, pp. 205-214 (2004).
Beckman et al., "The free radical theory of aging matures", *Physiol. Rev.*, vol. 78, pp. 547-581 (1998).
Budanov et al., "Regeneration of peroxiredoxins by p53-regulated sestrins, homologs of bacterial AhpD", *Science*, vol. 304, 596-600 (2004).
Cardullo et al., "Detection of nucleic acid hybridization by nonradiative fluorescence resonance energy transfer", *Proc. Natl. Acad. Sci.* vol. 85, pp. 8790-8794 (1998).
Debouck et al., "DNA microarrays in drug discovery and development", *in supplement to Nature Genetics*, vol. 21, pp. 48-50 (1990).
Finkel et al., "Oxidants, oxidative stress and the biology of ageing", *Nature*, vol. 408, pp. 239-247 (2000).
Fodor et al. "Light-directed, spatially addressable parallel chemical synthesis", *Science*, vol. 251, pp. 767-773 (1991).
Giusti et al., "Synthesis and characterization of 5'-fluorescent-dye-labeled oligonucleotides", *PCR Methods and Applications*, vol. 2, pp. 223-227 (1993).
Guyton et al., "Activation of mitogen-activated protein kinase by H2O2", *J. Biol. Chem.*, vol. 271, pp. 4138-4142 (1996).

(Continued)

*Primary Examiner*—Robert Havlin
(74) *Attorney, Agent, or Firm*—Morgan, Lewis & Bockius LLP; Jeffry S. Mann

(57) ABSTRACT

The present invention provides a novel class of fluorogenic probes for reactive oxygen species. Exemplary probes of the invention utilize a boronate deprotection mechanism to provide high selectivity and optical dynamic range for detecting $H_2O_2$ in aqueous solution over similar reactive oxygen species (ROS) including superoxide, nitric oxide, tert-butyl hydroperoxide, and hydroxyl radical; Peroxyresorufin-1 (PR1), Peroxyfluor-1 (PF1), and Peroxyxanthone-1 (PX1) are first-generation probes that respond to $H_2O_2$ by an increase in red, green, and blue fluorescence, respectively. The boronate dyes are cell-permeable and can detect micromolar changes in $H_2O_2$ concentrations in living cells, including hippocampal neurons, using confocal and two-photon microscopy. The unique combination of ROS selectivity, membrane permeability, and a range of available excitation/emission colors establishes the potential value of PR1, PF1, PX1, and related probes for interrogating the physiology and pathology of cellular $H_2O_2$.

18 Claims, 15 Drawing Sheets

OTHER PUBLICATIONS

Hammett, "The effect of structure upon the reactions of organic compounds, benzene derivatives", *J. Am. Chem. Soc.* vol. 59, p. 96 (1937).

Hansch et al., "Aromatic' substituen constants for structure-activity correlations", *J. Med. Chem.* vol. 15, pp. 1207 (1973).

Heller, "Electrical wiring of redox enzymes", *Acc. Chem. Res.*, vol. 23, p. 128 (1990).

Hempel et al., "Dihydrofluorescein diacetate is superior for detecting intracellular oxidants: Comparison with 2',7'-dichlorodihydrofluorescein diacetate, 5(and 6)-carboxy-2',7'-dichlorodihydrofluorescein diacetate, and dihydrorhodamine 123", *Free Rad. Biol. Med.* vol. 27, pp. 146-159 (1999).

Hickman et al., "Rational pattern design for in vitro cellular networks using surface photochemistry", *J. Vac. Sci. Technol.* vol. 12, pp. 607-616 (1994).

Hochstrasser et al., "Distance distribution in a dye-linked oligonucleotide determined by time-resolved fluorescence energy transfer", *Biophysical Chemistry*, vol. 45, pp. 133-141 (1992).

Keston et al., "The fluorometric analysis of ultramicro quantities of hydrogen peroxide", *Anal. Biochem.*, vol. 11, pp. 1-5 (1966).

Khrapko, et al., "A method for DNA sequencing by hybridization with oligonucleotide matrix", *DNA Sequence*, vol. 1, pp. 375-388 (1991).

Kleinfield et al., "Controlled outgrowth of dissociated neurons on patterned substrates", *J. Neurosci.*, vol. 8, pp. 4098-4120 (1998).

Kozhevnikov et al., "Strong emission increase of a dicarboxyterpyridene europium (III) complex in the presence of citrate and hydrogen peroxide", *Inong. Chim. Acta*, vol. 358, pp. 2445-2448 (2005).

Kulmala et al, "Electrochemiluminescent labels for applications in fully aqueous solutions at oxide-covered aluminium electrodes", *Analytica Chimica Acta*, vol. 386, p. 1 (1999).

Kumar et al., "Patterning self-assembled monolayers: Applications in materials science", *Langmuir*, vol. 10, pp. 1498-1511 (1994).

Kwon et al., "Reversible oxidation and inactivation of the tumor suppressor PTEN in cells stimulated with peptide growth factors", *Proc. Nat: Acad. Sci.*, vol. 101, pp. 16419-16424 (2004).

Lee et al., "Reversible inactivation of protein-tyrosine phosphatase 1B in A431 cells stimulated with epidermal growth factor", *J. Biol. Chem.*, vol. 273, pp. 15366-15372 (1998).

Lehrach et al., "Hybridization Fingerprinting in Genome Mapping and Sequencing", *Genome Analysis*, vol. 1, (1990).

Leslie et al., "Redox regulation of PI 3-kinase signalling via inactivation of PTEN", *EMBO J.*, vol. 22, pp. 5501-5510 (2003).

Levine et al., "Isolation and characterization of a photoprotein, 'phialidin', and a spectrally unique green-fluorescent protein from the bioluminscent jellyfish *Phialidium gregarium*" *Comp. Biochem. Physiol.*, vol. 72B, pp. 77-85 (1982).

Lo et al., "Development of highly selective and sensitive probes for hydrogen peroxide", *Chem. Commun.*, vol. 21, pp. 2728-2729 (2003).

Lo et al., "Involvement of reactive oxygen species in cytokine and growth factor induction of c-fos expression in chondrocytes", *J. Biol. Chem.*, vol. 270, pp. 11727-11730 (1995).

Maeda et al., "Fluorescent probes for hydrogen peroxide based on a non-oxidative mechanism", *Angew. Chem., Int. Ed.*, vol. 43, pp. 2389-2391 (2004).

Nelson et al., "Bifunctional oligonucleotide probes synthesized using a novel CPG support are able to detect single base pair mutations", *Nucleic Acids Research*, vol. 17, pp. 7187-7194 (1989).

Ohshima et al., "Chemical basis of inflammation-induced carcinogenesis", *Arch. Biochem. Biophys.*, vol. 417, pp. 3-11 (2003).

Onoda et al., "Fluorescence enhancement by hydroperoxides based on a change in the intramolecular charge transfer character of benzofurazan", *Chem. Commun.* pp. 1848-1850 (2005).

Onoda et al., "First fluorescent photoinduced electron transfer (PET) reagent for hydroperoxides", *Org. Lett.*, vol. 5, pp. 1459-1461 (2003).

Raju et al., "A fluorescent indicator for measuring cytosolic free magnesium", *Am. J. Physiol.*, vol. 256, pp. C540 (1989).

Riehl et al., "Circularly polarized luminescence spectroscopy", *Chem. Rev.* vol. 86, pp. 1 (1986).

Schmidt et al., "The roles of hydrogen peroxide and superoxide as messengers in the activation of transcription factor NF-KB", *Chem. Biol.*, vol. 2, pp. 13-22 (1995).

Selvin, "Fluorescence resonance energy transfer", P., *Methods in Enzymology*, vol. 246, pp. 300-334 (1995).

Setsukinai et al., "Development of novel fluorescence probes that can reliably detect reactive oxygen species and distinguish specific species", *J. Biol. Chem.*, vol. 278, pp. 3170-3175 (2003).

Shah et al, "Free radicals and redox signalling in cardiovascular disease", *Heart*, vol. 90, pp. 486-487(2004).

Sharma et al., "A general method for the synthesis of 3'-sulfhydryl and phosphate group containing oligonucleotides", *Nucleic Acids Research*, vol. 19, p. 3019 (1991).

Soh et al., "Design and development of a fluorescent probe for monitoring hydrogen peroxide using photoinduced electron transfer", *Bioorg. Med. Chem.*, vol. 13, pp. 1131-1139 (2005).

Southern et al. "Analyzing and comparing nucleic acid sequences by hybridization to arrays of oligonucleotides: Evaluation using experimental models", *Genomics*, vol. 13, pp. 1008-1017 (1992).

Sproat et al., "The synthesis of protected 5'-mercapto-2,5'-dideoxyribonucleoside-3'-O-phosphoramidites; uses of 5'-mercapto-2,5'-dideoxyribonucleotides", *Nucleic Acids Research*, vol. 15, pp. 4837 (1987).

Steinberg, I., "Long-range nonradiative transfer of electronic excitation energy in proteins and polypeptides", *Ann. Rev. Biochem.*, vol. 40, pp. 83-114 (1971).

Stone, "An assessment of proposed mechanisms for sensing hydrogen peroxide in mammalian systems", *Arch. Biochem. Biophys.*, vol. 422, pp. 119-124 (2004).

Stryer, "Fluorescence energy transfer as a spectroscopic ruler", L. *Ann. Rev. Biochem.*, vol. 47, pp. 819-846 (1978).

Wang et al., "Rapid sizing of short tandem repeat alleles using capillary array electrophoresis and energy-transfer fluorescent primers", *Anal. Chem.* vol. 67, pp. 1197-1203 (1995).

Wang et al., "Design and synthesis of new fluorogenic HIV protease substrates based on resonance energy transfer", *Tetrahedron Letters*, vol. 31, pp. 6493-6496 (1990).

Ward et al., "Spectral perturbations of the *Aequorea* green-fluorescent protein", *Photochem. Photobiol.* vol. 35, pp. 803-808 (1982).

Wilbanks et al., "Rod structure of a phycoerythrin II-containing Phycobilisome", *J. Biol. Chem.* vol. 268, pp. 1226-1235 (1993).

Wolfbeis et al., "A europium-ion-based luminescent sensing probe for hydrogen peroxide", *Angew. Chem., Int. Ed.*, vol. 41, pp. 4495-4498 (2002).

Woo et al., "Reversing the inactivation of peroxiredoxins caused by cystein sulfinic acid formation", *Science*, vol. 300, pp. 653-656 (2003).

Wood et al., "Peroxiredoxin evolution and the regulation of hydrogen peroxide signaling", *Science*, vol. 300, pp. 650-653 (2003).

Xia, Y., "Use of controlled reactive spreading of liquid alkanethiol on the surface of gold to modify the size of features produced by microcontact printing", *J. Am. Chem. Soc.* vol. 117, pp. 3274-3275 (1995).

Zhou et al., "A stable nonfluorescent-derivative of resorufin for the fluorometric determination of trace hydrogen peroxide: Applications in detecting the activity of phagocyte NADPH oxidase and other oxidases", *Anal. Biochem.*, vol. 253, pp. 162-168 (1997).

Zuckerman et al., "Efficient methods for attachment of thiol specific probes to the 3'-ends of synthetic oligodeoxyribonucleotides", *Nucleic Acids Research*, vol. 15, pp. 5305-5321 (1987).

\* cited by examiner

FLUOROGENIC PROBES FOR REACTIVE OXYGEN SPECIES

CROSS-REFERENCE TO RELATED APPLICATIONS

This application claims the benefit of Provisional Patent Application No. 60/731,085, filed Oct. 27, 2005, which is incorporated by reference herein in its entirety for all purposes.

BACKGROUND OF THE INVENTION

Many diseases associated with human aging, including cancer (Ohshima et al., *Arch. Biochem. Biophys.* 2003, 417, 3-11), cardiovascular disorders (Shah et al., *Heart* 2004, 90, 486-487), and neurodegenerative diseases (Barnham et al., *Nat. Rev. Drug Discovery* 2004, 3, 205-214; Connor, J. R.; Editor *Metals and Oxidative Damage in Neurological Disorders*, 1997) have a strong oxidative stress component, but the basic molecular mechanisms that connect aging, age-related diseases, and oxidative stress remain insufficiently understood (Aruoma et al., Editors *Molecular Biology of Free Radicals in Human Diseases*, 1998; Balaban et al., *Cell* 2005, 120, 483-495; Finkel et al., *Nature* 2000, 408, 239-247). Oxidative stress is the result of unregulated production of reactive oxygen species (ROS), and cellular mismanagement of oxidation-reduction chemistry can trigger subsequent oxidative damage to tissue and organs (Beckman et al., *Physiol. Rev.* 1998, 78, 547-581). In particular, hydrogen peroxide is a major ROS by-product in living organisms and a common marker for oxidative stress. The chemical biology of $H_2O_2$ is much more complex, however, as mounting evidence also supports a role for $H_2O_2$ as a second messenger in normal cellular signal transduction (Rhee et al., *Curr. Opin. Cell Biol.* 2005, 17, 183-189; Finkel, T. *Curr. Opin. Cell Biol.* 2003, 15, 247-254; Stone, *Arch. Biochem. Biophys.* 2004, 422, 119-124; Wood et al., *Science* 2003, 300, 650-653). Peroxide bursts in response to cell receptor stimulation can affect several classes of essential signaling proteins that control cell proliferation and/or cell death. Included are kinases like the mitogen-activated protein (MAP) kinase family (Guyton et al., *J. Biol. Chem.* 1996, 271, 4138-4142), transcription factors such as nuclear factor κB (NF-κB) (Schmidt et al., *Chem. Biol.* 1995, 2, 13-22), and activating protein 1 (AP-1) (Lo et al., *J. Biol. Chem.* 1995, 270, 11727-11730) as well as various protein tyrosine phosphatases (PTPs) (Lee et al., *J. Biol. Chem.* 1998, 273, 15366-15372; Kwon et al., *Proc. Nat. Acad. Sci. USA* 2004, 101, 16419-16424; Leslie et al., *EMBO J.* 2003, 22, 5501-5510) ion channels (Avshalumov et al., *Proc. Nat. Acad. Sci. USA* 2003, 100, 11729-11734; Avshalumov et al., *J. Neurosci.* 2005, 25, 4222-4231) and G proteins. Despite the far-ranging consequences of $H_2O_2$ in human physiology and pathology, mechanistic details surrounding intracellular $H_2O_2$ generation, trafficking, and function remain elusive even in the simplest eukaryotic organisms.

Fluorescent probes are well suited to meet the need for tools to map the spatial and temporal distribution of $H_2O_2$ within living cells. Such reagents have revolutionized the study of calcium in biological systems and hold much promise for enhancing our understanding of $H_2O_2$ physiology and pathology. The major challenge for practical $H_2O_2$ sensing in biological environments is creating water-soluble systems that respond to $H_2O_2$ selectively over competing cellular ROS such as superoxide ($O_2^-$), nitric oxide (NO), and lipid peroxides. Several types of small-molecule reporters have been described for $H_2O_2$ detection. Included are dihydro derivatives of common fluorescent dyes (e.g., 2',7'-dichlorodihydrofluorescein, DCFH, and dihydrorhodamine 123, DHR) (Negre-Salvayre et al., *Meth. Enzymol.* 2002, 352, 62-71; Hempel et al., *Free Rad. Biol. Med.* 1999, 27, 146-159; Keston et al., *Anal. Biochem.* 1965, 11, 1-5; Haugland, R. P. *The Handbook: A Guide to Fluorescent Probes and Labeling Technologies;* 10th ed.; Invitrogen/Molecular Probes: Carlsbad, Calif., 2005), the Amplex Red/peroxidase system (Zhou et al., *Anal. Biochem.* 1997, 253, 162-168) phosphine-containing fluorophores (Akasaka et al., *Anal. Lett.* 1987, 20, 797-807; Onoda et al., *Org Lett.* 2003, 5, 1459-1461; Onoda et al., *Chem. Commun.* 2005, 1848-1850; Soh et al., *Bioorg. Med. Chem.* 2005, 13, 1131-1139) luminescent lanthanide complexes (Wolfbeis et al., *Angew. Chem., Int. Ed.* 2002, 41, 4495-4498; Kozhevnikov et al., *Inorg. Chim. Acta* 2005, 358, 2445-2448 and chromophores with ROS-cleavable protecting groups (Maeda et al., *Angew. Chem., Int. Ed.* 2004, 43, 2389-2391; Lo et al., *Chem. Commun.* 2003, 2728-2729; Setsukinai et al., *J. Biol. Chem.* 2003, 278, 3170-3175). Limitations of these and other currently available $H_2O_2$-responsive probes include interfering background fluorescence from competing ROS, potential side reactions with thiols that are present in high concentrations within cells, the need for external activating enzyme, lack of membrane permeability, and/or lack of water solubility or compatibility, requiring the use of organic co-solvents.

SUMMARY OF THE INVENTION

Luminescent (including fluorescent and phosphorescent) markers find a wide variety of applications in science, medicine and engineering. In many situations, these markers provide competitive replacements for radiolabels, chromogens, radiation-dense dyes, etc. Moreover, improvements in fluorimetric instrumentation have increased attainable sensitivities and permitted quantitative analysis.

It has now been discovered that conversion of a pro-fluorescent species into a fluorescent probe by chemoselective deprotection of the pro-fluorescent species can be utilized to observe and quantitate the presence and amount of an analyte of interest in an assay. In an exemplary embodiment, compounds of the invention are of use to detect the presence of and elucidate the complex roles of oxidants, e.g., $H_2O_2$, in living systems. The compounds of the invention are selective and sensitive chemosensors for $H_2O_2$ with properties amenable to biological imaging applications. For example, the fluorescent reporting group is biologically compatible, has a near unity quantum yield, and a sizeable extinction coefficient. Additionally, its visible excitation and emission profiles limit photodamage to biological samples, avoid autofluorescence from native cellular species, and offer compatibility with common optical filter sets for fluorescence microscopy An exemplary mechanism of deprotection, which converts the fluorogenic species into a fluorophore is chemoselective boronate deprotection. Compounds of the invention that operate according to this detection mechanism, which relies on chemoselective boronate deprotection rather than non-specific oxidation to provide an optical response. Initial experiments establish that the compounds of the invention are highly selective for $H_2O_2$ and can be loaded passively into living cells and report changes in intracellular $H_2O_2$ concentrations. The resulting probe platforms feature excellent selectivity for $H_2O_2$ over competing ROS in aqueous solution and excitation/emission profiles that span the ultraviolet to visible region. Moreover, these probes are capable of imaging micromolar changes in $H_2O_2$ concentrations in living cells, including hippocampal neurons from primary culture, using confocal and two-photon microscopy.

Accordingly, in a first aspect, the invention provides pro-fluorescent compounds according to Formula I:

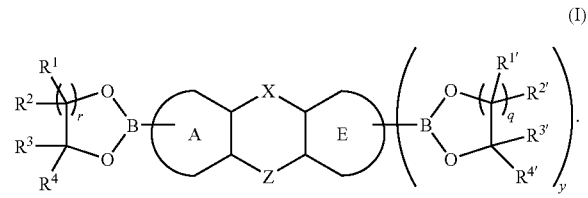

In Formula I, A and E represent moieties that are independently selected from substituted or unsubstituted aryl and substituted or unsubstituted heteroaryl rings. The symbols X and Z represent members independently selected from $CR^5R^6$, $C(O)$, $NR^5$ and substituted or unsubstituted heterocycloalkyl. $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^6$ is H, CN, $COR^7$, $OR^8$, substituted or unsubstituted alkyl or substituted or unsubstituted heteroalkyl, in which $R^7$ is $OR^9$ or $NR^9R^{10}$. The symbols $R^9$ and $R^{10}$ represent groups that are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^8$ represents H, substituted or unsubstituted alkyl, substituted or unsubstituted heteroalkyl, substituted or unsubstituted aryl, substituted or unsubstituted heteroaryl or substituted or unsubstituted heterocycloalkyl. The index y represents an integer selected from 0 and 1. The indices q and r are members independently selected from 1, 2 and 3. The symbols $R^1$, $R^{1'}$, $R^2$, $R^{2'}$, $R^3$, $R^{3'}$, $R^4$ and $R^{4'}$ independently represent H, substituted or unsubstituted alkyl, or substituted or unsubstituted heteroalkyl.

Also provided are methods for detecting a selected analyte utilizing a compound of the invention and kits containing one or more compound of the invention and directions for using the compound of the invention to detect a selected analyte.

Further objects, advantages and aspects of the compounds and methods of the present invention are set forth in the detailed description that follows.

DETAILED DESCRIPTION OF THE INVENTION AND THE PREFERRED EMBODIMENTS

Abbreviations

Figure 1:
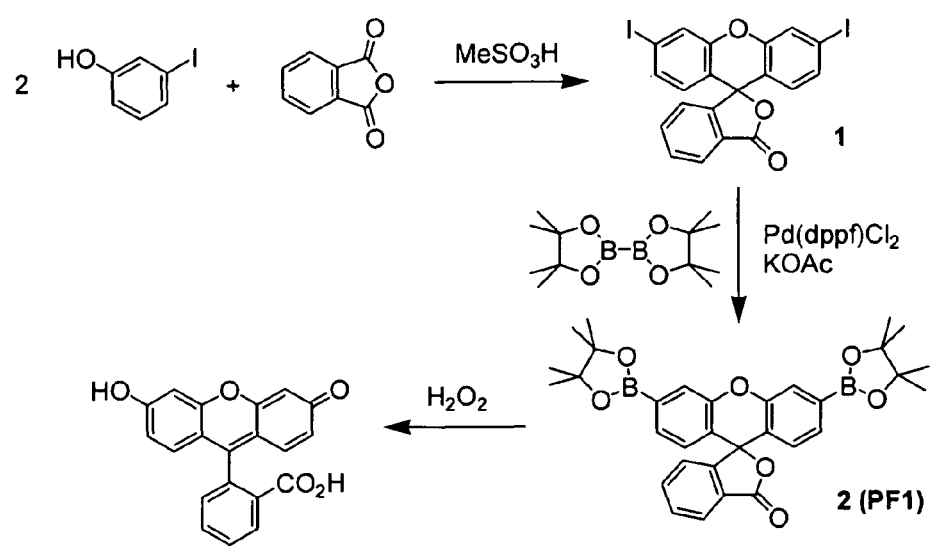
FIG. 1 is an exemplary synthetic scheme for the preparation of a probe of the invention.

As used herein, "ROS," refers to reactive oxygen species, including but not limited to peroxides, oxygen free radicals and the like.

Definitions

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and nucleic acid chemistry and hybridization described below are those well known and commonly employed in the art. Standard techniques are used for nucleic acid and peptide synthesis. The nomenclature used herein and the laboratory procedures in analytical chemistry, and organic synthetic described below are those known and employed in the art. Standard techniques, or modifications thereof, are used for chemical syntheses and chemical analyses.

"Analyte", as used herein, means any compound or molecule of interest for which a diagnostic test is performed, such as a biopolymer or a small molecular bioactive material. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a group of molecules that form a single complex within which energy transfer occurs. Such complexes may comprise, for example, two fluorescent groups, which may be different from groups and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

"Fluorescence resonance energy transfer" or "FRET" is used interchangeably with FET, and refers to an energy transfer phenomenon in which the light emitted by the excited fluorescent group is absorbed at least partially by a fluorescence-modifying group of the invention. If the fluorescence-modifying group is a quenching group, then that group will preferably not radiate a substantial fraction of the absorbed light as light of a different wavelength, and will preferably dissipate it as heat. FRET depends on an overlap between the emission spectrum of the fluorescent group and the absorption spectrum of the quenching group. FRET also depends on the distance between the quenching group and the fluorescent group.

As used herein, "fluorophore" refers to a fluorescent species other than a TIAM complex of the invention.

"Moiety" refers to the radical of a molecule that is attached to another moiety.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a PL, a fluorophore or another moiety.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A.

F., in CHEMISTRY AND BIOCHEMISTRY OF AMINO ACIDS, PEPTIDES AND PROTEINS, B. Weinstein, eds., Marcel Dekker, New York, p. 267 (1983).

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, sulfonate, thiosulfate, and thiosulfonate.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is (1) able to direct the entity to which it is attached (e.g., therapeutic agent or marker) to a target cell, for example to a specific type of tumor cell or (2) is preferentially activated at a target tissue, for example a tumor. The targeting group can be a small molecule, which is intended to include both non-peptides and peptides. The targeting group can also be a macromolecule, which includes saccharides, lectins, receptors, ligand for receptors, proteins such as BSA, antibodies, and so forth.

The symbol , whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl."

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quatemized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Substituents for alkyl and heteroalkyl moieties are selected from the group of acceptable "alkyl moiety substituents" and "heteroalkyl moiety substituents" described below.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable "aryl moiety substituents" and "heteroaryl moiety substituents" described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R''' and R'''' groups when more than one of these groups is present.

Two of the substituents on adjacent atoms may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms may optionally be replaced with a substituent of the formula -A-(CH$_2$)$_r$—B—, wherein A and B are independently —CRR'—, —O—, —NR'—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

Introduction

The present invention provides a class of pro-fluorescent and fluorescent probes. The compounds of the invention emit light or, alternatively, they can be used to absorb light emitted by a reporter fluorophore. The fluorophores of the invention can be used as small molecules in solution assays or they can be utilized as a label that is conjugated to an analyte or a species that interacts with, and allows detection and/or quantification of an analyte. An exemplary pro-fluorescent probe of the invention is converted to the corresponding fluorophore through chemoselective removal of a moiety, the removal of which causes the conversion of the profluorescent compound into the corresponding fluorescent compound.

The compounds of the present invention provide numerous advantages. For example, fluorescent probes have the advantage of requiring few precautions in their handling, and being amenable to high-throughput visualization techniques (optical analysis including digitization of the image for analysis in an integrated system comprising a computer). Preferred probes are typically characterized by one or more of the following: chemospecific conversion from fluorogen to fluorophore, high sensitivity, high stability, low background emission, long lifetimes, low environmental sensitivity and high specificity in labeling.

The compounds of the invention can be used as probes, e.g., in microscopy, enzymology, clinical chemistry, histochemistry, molecular biology and medicine. The probes of the invention are also useful as therapeutic agents in modalities, such as photodynamic therapy and as diagnostic agents in imaging methods, such as magnetic resonance imaging, positron emission tomography, near infrared imaging and the like. The fluorogens of the invention are also useful components of devices and methods for measuring oxidases, e.g., glucose oxidase, amine oxidase, peroxidase, etc. Moreover, the compounds of the invention are useful as components of optical amplifiers of light, waveguides and the like. Furthermore, the compounds of the invention can be incorporated into inks and dyes, such as those used in the printing of currency or other negotiable instruments.

When the fluorogens of the invention are converted to the corresponding fluorophores, these compounds can be made to luminesce by exciting them in any manner known in the art, including, for example, with light or electrochemical energy (see, for example, Kulmala et al, *Analytica Chimica Acta* 386: 1 (1999)). The luminescence can, in the case of chiral compounds of the invention, be circularly polarized (see, for example, Riehl et al., *Chem. Rev.* 86: 1 (1986)).

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

The Compounds

The present invention exploits the discovery that chemoselective removal of a moiety from a pro-fluorescent compound can convert that compound into a fluorescent probe. When the moiety is removed by an analyte or product of an analyte, the compounds of the invention are of particular use in assays for the analyte. Though the present invention is exemplified by reference to chemoselective removal of a boronate moiety, the invention is not limited to the use of any one particular removable moiety. The art is replete with synthetic methodologies for preparing compounds that include groups susceptible to cleavage under specific conditions, e.g., oxidation, reduction, nucleophilic and electrophilic substitutions, electrolysis, photolysis and the like. In general, methodologies for the chemoselective deprotection of organic compounds are of use in the present invention. Accordingly, the present invention broadly provides a class of pro-fluorescent compounds that are converted into fluorophores by the action of a selected analyte or product of a selected analyte.

Probes for ROS

In an exemplary embodiment, the fluorogenic compounds of the invention include within their structure one or more moiety that is removed by a reactive oxygen species, e.g., oxygen, peroxide, superoxide, hydroxyl radical, hypochlorite, etc. The present invention is further illustrated by reference to a representative class of probes that is activated (i.e., converted to a fluorescent species) by hydrogen peroxide, providing a uniform class of red-, green-, blue-fluorescent probes. As will be apparent to those of skill in the art, the instant invention is not limited to the use of hydrogen peroxide as an activating agent.

Hydrogen peroxide is a major reactive oxygen species (ROS) in living organisms, and its homeostasis can have diverse physiological and pathological consequences (Gutteridge, *Free Radicals in Biology and Medicine,* 3rd Ed.; Clarendon Press: Oxford, UK, 1999). $H_2O_2$ is a source of oxidative stress, (Finkel, *Curr. Opin. Cell Biol.* 2003, 15, 247-254) and oxidative damage resulting from cellular imbalance of $H_2O_2$ and other ROS oxidants is connected to aging and severe human diseases such as cancer (Ohshima et al., *Arch. Biochem. Biophys.* 2003, 417, 3-11), cardiovascular disorders (Shah et al., *Heart* 2004, 90, 486-487) and Alzheimer's and related neurodegenerative diseases (Barnham et al., *Nature Rev. Drug Disc.* 2004, 3, 205-214). On the other hand, emerging evidence supports a physiological role for $H_2O_2$ as a second messenger in cellular signal transduction (Wood et al., *Science* 2003, 300, 650-653; Woo et al., *Science* 2003, 300, 653-656; Budanov et al., *Science* 2004, 304, 596-600). For example, peroxide bursts trigger mitogen-activated protein (MAP) kinase (Guyton et al., *J. Biol. Chem.* 1996, 271, 4138-4142 and nuclear factor κB (NF-κB) pathways that affect cell proliferation and cell death (Schmidt et al., *Chem. Biol.* 1995, 2, 13-22).

Despite the importance of $H_2O_2$ to human health and disease, the molecular mechanisms of its production, accumulation, trafficking, and function are insufficiently understood even in the simplest eukaryotic organisms. Accordingly, interest in developing new chemical tools to study the physiological and pathological roles of $H_2O_2$ and related ROS in living systems is widespread. In this regard, fluorescent probes are well suited to meet the need for reagents to interrogate the cellular chemistry of $H_2O_2$ at the molecular level. One major challenge to achieving this goal is creating water-soluble systems that report $H_2O_2$ selectively over competing cellular ROS like superoxide ($O_2^-$), nitric oxide (NO), and lipid alkylperoxides. Synthetic small molecules offer one approach to such probes, and several types of reagents have been examined for $H_2O_2$ detection. Included are dihydro analogs of fluorescent dyes (e.g., 2',7'-dichlorodihydrofluorescein (DCFH), Amplex Red, dihydrorhodamine 123) (Negre-Salvayre et al., *Meth. Enzymol.* 2002, 352, 62-71), phosphine-based fluorophores (Akasaka et al., *Anal. Lett.* 1987, 20, 731-745), lanthanide coordination complexes (Wolfbeis et al., *Angew. Chem. Int. Ed.* 2002, 41, 4495-4498), and chromophores with ROS-cleavable protecting groups (Setsukinai et al., *J. Biol. Chem.* 2003, 278, 3170-3175). However, limitations of currently available $H_2O_2$-responsive probes include interfering background fluorescence from other ROS, the need for an external activating enzyme, lack of water solubility or compatibility, and/or excitation profiles in the ultraviolet region, which can damage living samples and cause interfering autofluorescence from native cellular species. The most commonly used fluorophore for cellular ROS detection, DCFH, is also easily autoxidized and exhibits increased background fluorescence upon continued exposure to light.

In an exemplary embodiment, the present invention provides an array of pro-fluorescent compounds that include at least one boronate moiety within their framework, such as those having a structure according to Formula I:

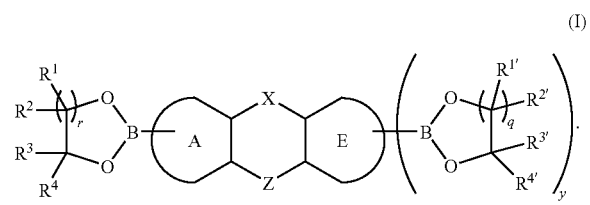

(I)

In Formula I, A and E represent moieties that are independently selected from substituted or unsubstituted aryl and substituted or unsubstituted heteroaryl rings. The symbols X and Z represent members independently selected from $CR^5R^6$, C(O), $NR^5$ and substituted or unsubstituted heterocycloalkyl. $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^6$ is H, CN, $COR^7$, $OR^8$, substituted or unsubstituted alkyl or substituted or unsubstituted heteroalkyl, in which $R^7$ is $OR^9$ or $NR^9R^{10}$. The symbols $R^9$ and $R^{10}$ represent groups that are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^8$ represents H, substituted or unsubstituted alkyl, substituted or unsubstituted heteroalkyl, substituted or unsubstituted aryl, substituted or unsubstituted heteroaryl or substituted or unsubstituted heterocycloalkyl. The index y represents an integer selected from 0 and 1. The indices q and r are members independently selected from 1, 2 and 3. The symbols $R^1$, $R^{1'}$, $R^2$, $R^{2'}$, $R^3$, $R^{3'}$, $R^4$ and $R^{4'}$ independently represent H, substituted or unsubstituted alkyl, or substituted or unsubstituted heteroalkyl.

In another exemplary embodiment, the invention provides a pro-fluorescent compound having the formula:

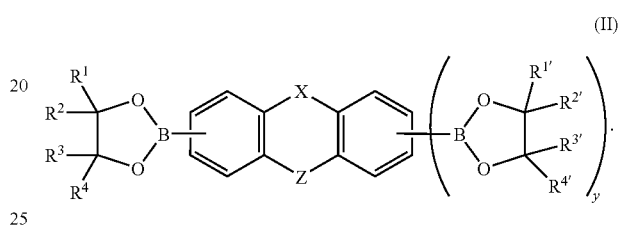

(II)

In a still further exemplary embodiment, the compound according to the invention has the formula:

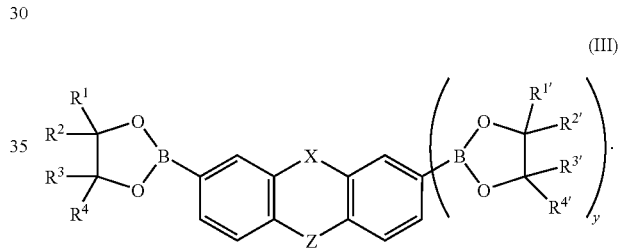

(III)

In yet another exemplary embodiment, the pro-fluorescent compound of the invention includes a lactam moiety. A representative compound according to this motif has the formula:

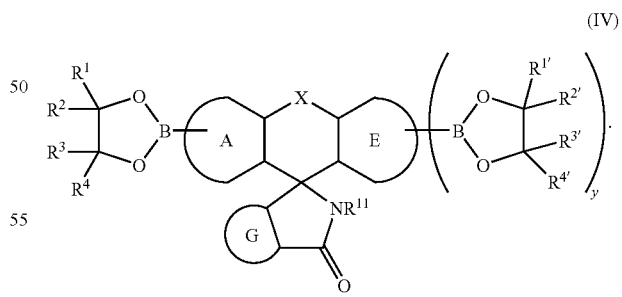

(IV)

G is a ring system selected from substituted or unsubstituted cycloalkyl, substituted or unsubstituted aryl and substituted or unsubstituted heteroaryl rings. R11 represents a member selected from H, substituted or unsubstituted alkyl and substituted or unsubstituted heteroalkyl.

In another exemplary embodiment, the invention provides a compound having the formula:

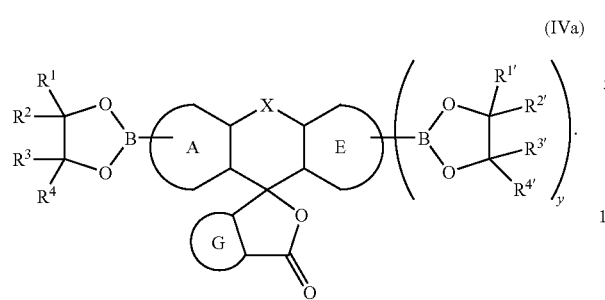

(IVa)

In an exemplary embodiment according to Formulae IV and IVa, G is a substituted or unsubstituted phenyl ring fused to the heterocycle.

In each of the Formulae set forth above, at least one of A, E or G can be substituted with one or more electron withdrawing, electron donating group and/or linker group, optionally attaching the compound to a carrier species. Those of skill in the art will understand which substituents, when appended to an aromatic ring will exhibit electron withdrawing or electron donating properties. Tables of substituents that are appropriate for inclusion in the compounds of the invention can be found in the literature. See, for example, Hammett, J. Am. Chem. Soc. 59: 96 (1937); Johnson, THE HAMMETT EQUATION, Cambridge University Press, New York, 1973; Hansch et al., J. Med. Chem. 16: 1207 (1973); and Hansch et al., SUBSTITUENT CONSTANTS FOR CORRELATION ANALYSIS IN CHEMISTRY AND BIOLOGY, Wiley, New York, 1979. Representative substituents are set forth hereinabove in the definition of the aryl and substituted aryl groups.

Furthermore, though Formulae II-IV include 5-member boronates, those of skill will appreciate that this is for clarity of representation: the boronate rings can be independently selected from 5-membered, 6-membered, 7-membered and higher ring systems. Exemplary compounds having boronates of various ring sizes, and their oxidized analogues, are shown below.

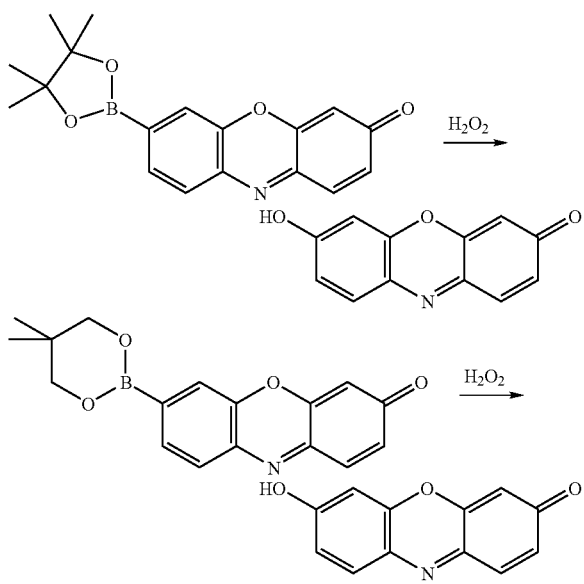

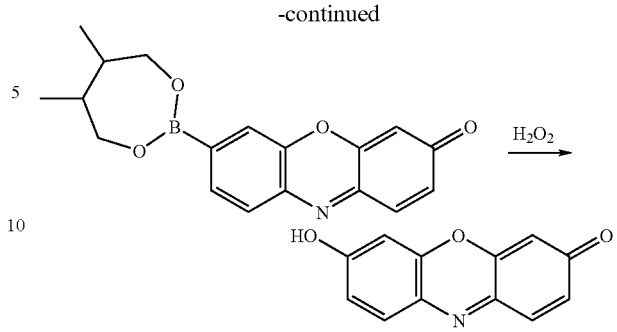

-continued

Selected compounds of the invention include one or more aryl or heteroaryl ring that is substituted with one or more halogen. Upon activation, compounds according to this motif provide enhanced fluorescent signal relative to the analogous non-halogenated compound. Moreover, the activated compound provides a fluorescence signal that is more stable over a prolonged period in the presence of a ROS, e.g., peroxide than is that of the corresponding non-halogenated compound. A presently preferred halogen is fluorine.

Moreover, the compounds of the invention can be connected to a carrier species e.g., biomolecule; a quencher or a fluorophore by a linker of substantially any length (zero-order or higher) and chemical composition. As such, representative linkers include, for example, substituted or unsubstituted alkyl groups, substituted heteroalkyl groups, conjugated unsaturated systems, aryl groups, heteroaryl groups, dendrimers, polyethers, polyamides, polyimines, biopolymers and linkers that are a combination of more than one of these groups. Other useful linkers will be apparent to those of skill in the art. The linker is generally attached to the compound of the invention (or its fluorescent analogue) through a linking group formed through reaction between a reactive group on the fluorogenic compound and a complementary reactive group on a linker arm precursor. The linker is attached to a carrier species through a similar reactive group. Similarly, a linking group binds the linker and carrier species.

For example, one or more of A, E and/or G is substituted with one or more linker that is selected from a primary alkyl amine, preferably a $C_1$ to $C_{10}$ alkyl chain bearing an amine moiety at the ω-position, more preferably a $C_2$ to $C_6$ alkyl chain bearing an amine moiety at the ω-position. Such a linker is of use to form conjugates with any carrier species that includes a reactive functional group that reacts with an amine moiety, e.g., an activated carboxyl moiety. An array of other strategies for attaching linkers to a useful probe and forming conjugates between the probe and a carrier species are known to those of skill in the art.

In compounds according to Formula IV, a linker is optionally attached to the nitrogen of the lactam ring. Thus, $R^{11}$ is optionally a linker as described above.

In another preferred embodiment, one or more of A, E and/or G is substituted with a moiety that includes a polyether, preferably a member selected from ethylene glycol, ethylene glycol oligomers and combinations thereof, having a molecular weight of from about 60 daltons to about 10,000 daltons, and more preferably of from about 100 daltons to about 1,000 daltons. The polyether can also be a component of a linker.

Representative polyether-based substituents include, but are not limited to, the following structures:

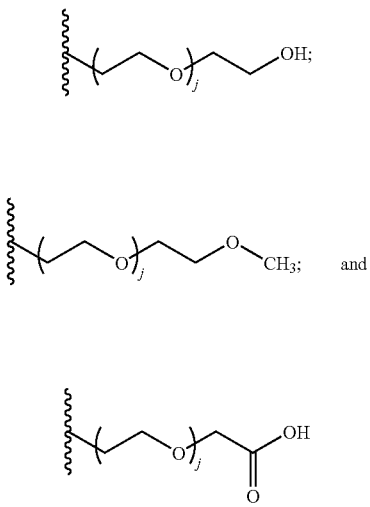

in which j is a number from 1 to 1,000, inclusive. Other functionalized polyethers are known to those of skill in the art, and many are commercially available from, for example, Shearwater Polymers, Inc. (Alabama).

In another preferred embodiment, one or more of the above-recited substituent groups includes a reactive group for conjugating the probe to a molecules or surface. Representative useful reactive groups are discussed in greater detail in the following sections. Additional information on useful reactive groups is known to those of skill in the art. See, for example, Hermanson, BIOCONJUGATE TECHNIQUES, Academic Press, San Diego, 1996.

In a preferred embodiment, one or more of the substituents on A, E and/or G, is a ω-carboxyl alkyl group or a ω-carboxyl substituted alkyl group. A representative substituent has a formula according to Formula V:

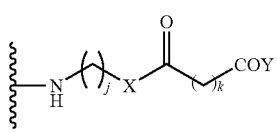

(V)

in which X is a member selected from O, S and $NR^{12}$. $R^{12}$ is preferably a member selected from H, alkyl and substituted alkyl. Y is preferably a member selected from $OR^{13}$, a halogen and a single negative charge. $R^{13}$ is H, substituted or unsubstituted alkyl, substituted or unsubstituted heteroalkyl, substituted or unsubstituted aryl or substituted or unsubstituted heteroaryl. The indices j and k integers independently selected from 1 to 18, preferably 2 to 16, more preferably 4 to 14.

$R^{11}$ may be a similar substituent. For example, in one embodiment, the terminal nitrogen atom in Formula V is the endocyclic nitrogen of the lactam, providing a substituent having the structure:

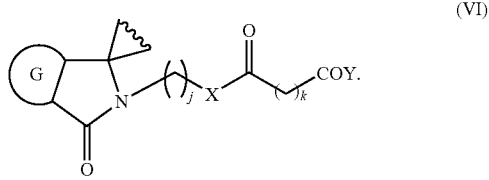

(VI)

In yet another exemplary embodiment, one or more of the substituents can combine characteristics of one or more of the above-recited groups. For example, an exemplary substituent combines both the attributes of a polyether and a reactive group:

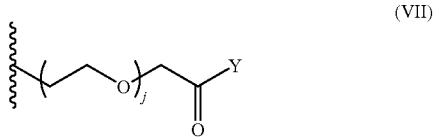

(VII)

in which j is an integer between 1 and 1,000, inclusive. Other such substituents include, but are not limited to, moieties such as sugars (e.g., polyol with reactive hydroxyl), amino acids, amino alcohols, carboxy alcohols, amino thiols, and the like.

In a still further preferred embodiment, the compounds of the invention have more than one type of substituent is present on a single molecule. For example a single molecule can include a polyether substituent and an alkylamine substituent. Many other such combinations of different substituents will be apparent to those of skill in the art.

In other embodiments a substituent on A, E or G is a fluorophore, quencher or fluorescence sensitizer. Exemplary sensitizers include rhodamine 560, 575 and 590 fluoresceins, 2- or 4-quinolones, 2 or 4-coumarins, or derivatives thereof e.g. coumarin 445, 450, 490, 500 and 503, 4-trifluoromethylcoumarin (TFC), 7-diethyl-amino-cumarin-3-carbohyddzide, etc., and especially carbostyril 124 (7-amino-4-methyl-2-quinolone), coumarin 120 (7-amino-4-methyl-2-coumarin), coumarin 124 (7-amino-4-(trifluoromethyl)-2-coumarin), aminomethyltrimethylpsoralen, napthalene and the like. In a preferred embodiment, the sensitizer is a moiety that comprises a napthyl moiety.

An exemplary compound according to this embodiment, it preparation and its use in a ratiometric detection scheme are shown below.

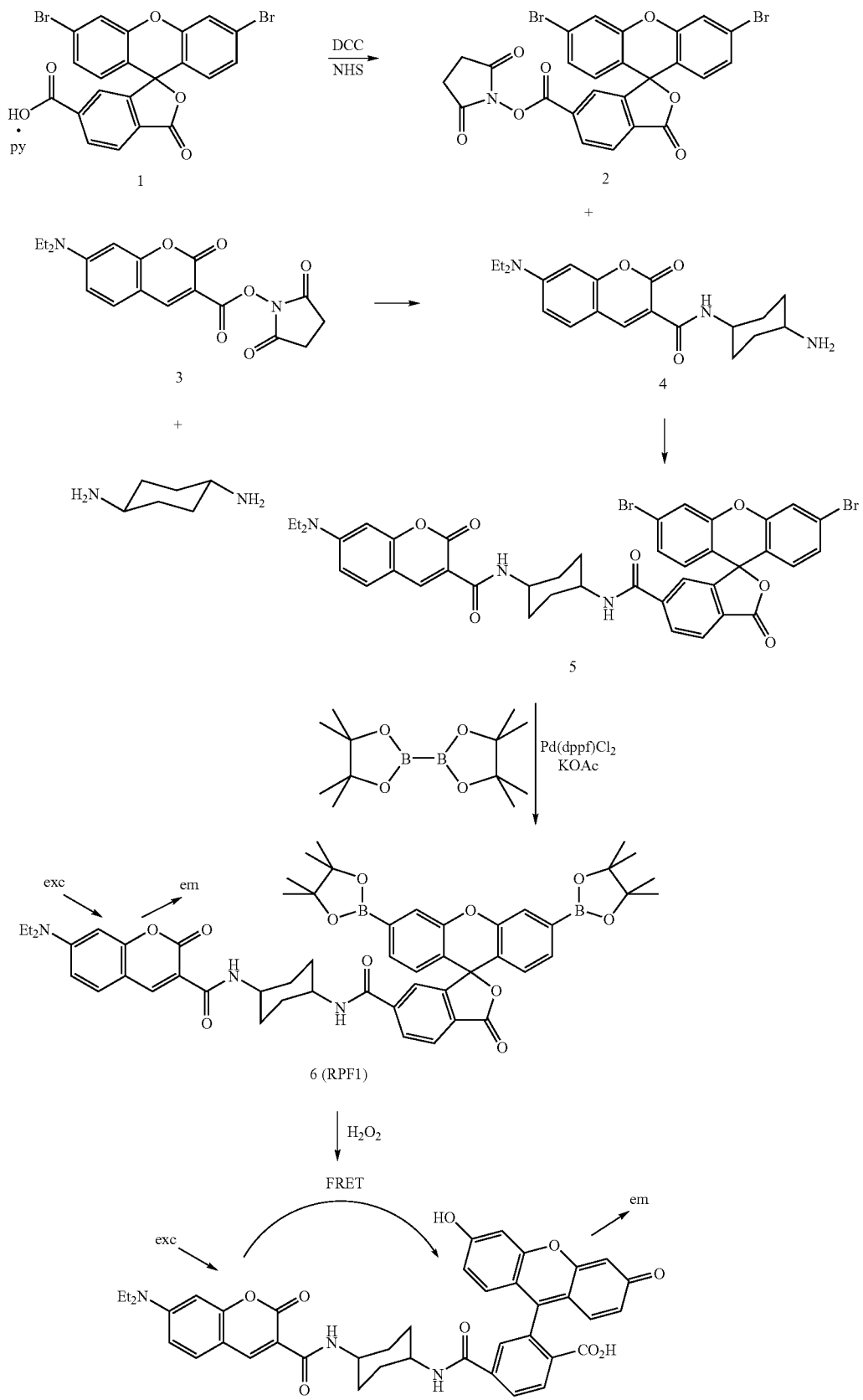

In an exemplary embodiment, compounds that include a boron-protected fluorophore conjugated to another flurorophore are of us for ratiometric detection of $H_2O_2$ and organic peroxides. The ratiometeric strategy is based on modulating fluorescence resonance energy transfer (FRET) in a two-fluorophore cassette comprised of a fluorophore (e.g., coumarin) donor and a boronate-protected fluorescein acceptor linked by a spacer (e.g., a ridid spacer). This approach to controlling FRET by electronic spectral overlap as opposed to modulating the physical separation of donor and acceptor dyes is inspired by optical reporters of phosphatase activity. In the absence of $H_2O_2$ or an organic peroxide, the boronate protecting groups force the acceptor to adopt a closed, colorless, and non-fluorescent lactone form. Spectral overlap between coumarin emission and fluorescein absorption is minimized, FRET is suppressed, and only blue donor emission is observed upon excitation of the coumarin chromophore. Upon selective reaction with peroxide to generate the open, colored, and fluorescent fluorescein moiety, the acceptor shows a strong absorption in the coumarin emission region. Spectral overlap is enhanced and excitation of the donor coumarin chromophore results in increased green fluorescein acceptor emission by FRET. Changes in peroxide concentration can be detected by measuring the ratio of blue and green fluorescence intensitites.

Thus, the present invention provides compounds and methods for use in ratiometric detection of peroxides. The compounds include a fluorophore conjugated through a linker to a boron-protected compound of the invention. The changes in peroxide concentration are detected by measuring a ratio of a first fluorescence signal and a second fluorescence signal.

In an exemplary embodiment, the linker is not an unsubstituted, unsaturated $C_5$-$C_7$ hydrocarbon ring. In another exemplary embodiment, the fluorophore conjugated to the boron-protected moiety is not coumarin. In still a further exemplary embodiment, the linker is not an unsubstituted, unsaturated $C_5$-$C_7$ hydrocarbon ring and the fluorophore conjugated to the boron-protected moiety is not coumarin. In yet another exemplary embodiment, the compound is other than the coumarin-linked conjugate labeled as 6 in the figure above.

The compounds of the invention, in their unconjugated form are useful as probes, indicators, separation media, and the like. Moreover, the compounds of the invention can be conjugated to a wide variety of compounds to create specific labels, probes, diagnostic and/or therapeutic reagents, etc. Examples of species to which the compounds of the invention can be conjugated include, for example, biomolecules such as, proteins (e.g., antibodies, enzymes, receptors, etc.), nucleic acids (e.g., RNA, DNA, etc.), bioactive molecules (e.g., drugs, toxins, etc.); solid substrates such as glass or polymeric beads, sheets, fibers, membranes (e.g. nylon, nitrocellulose), slides (e.g. glass, quartz) and probes; etc.

In another exemplary embodiment, a compound of the invention is utilized to detect a peroxide component of an explosive, e.g., an improvised explosive device. The compounds of use in this modality can be free or immobilized on a solid support, e.g., a test strip, dip stick, lateral flow chromatography device, and the like. The compounds so immobilized can be adsorbed onto the solid support or can be covalently attached thereto.

Reactive Functional Groups

Certain of the compounds of the invention bear a reactive functional group, such as a component of a linker, which can be located at any position on any aryl nucleus or on a chain, such as an alkyl chain, attached to an aryl nucleus, or on the backbone of the chelating agent. These compounds are referred to herein as "reactive ligands." When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions available with reactive ligands of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to esters, sulfonates, ethers, aldehydes, etc.
(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides or reacted with acyl halides;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

The reactive functional groups can be chosen such that they do not participate in, or interfere with, the reactions necessary to assemble the reactive ligand. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Carrier Species

In an exemplary embodiment, a reactive functional group is utilized to attach a compound of the invention to a carrier species, converting the reactive functional group to a linking group between the fluorogenic compound and the carrier species.

Representative carrier species include, but are not limited to species that include an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a solid support, a polymeric microparticle, a biological cell, a virus and combinations thereof. In another exemplary embodiment, the carrier species is selected from a hapten, a nucleotide, an oligonucleotide, a nucleic acid polymer, a protein, a peptide or a polysaccharide. In a preferred embodiment the carrier species is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier species is an antibody or fragment thereof, an antigen, an avidin or streptavidin, a biotin, a dextran, an antibody binding protein, a fluorescent protein, agarose, and a non-biological microparticle. Typically, the carrier species is an antibody, an antibody fragment, antibody-binding proteins, avidin, streptavidin, a toxin, a lectin, or a growth factor. Preferred haptens include biotin, digoxigenin and fluorophores.

Exemplary antibody binging proteins include protein A, protein G, soluble Fc receptor, protein L, lectins, anti-IgG, anti-IgA, anti-IgM, anti-IgD, anti-IgE or a fragment thereof.

In another exemplary embodiment, the carrier species is an amino acid (including those that are protected or are substituted by phosphates, carbohydrates, or $C_1$ to $C_{22}$ carboxylic acids), or a polymer of amino acids such as a peptide or protein. Exemplary carrier species include at least five amino acids, and preferably from 5 to 36 amino acids.

Exemplary peptides include, but are not limited to, neuropeptides, cytokines, toxins, protease substrates, and protein kinase substrates. Other exemplary peptides may function as organelle localization peptides, targeting the conjugated compound for localization within a particular cellular substructure by cellular transport mechanisms.

In another exemplary embodiment, the carrier species comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier species is a nucleoside or a deoxynucleoside or a dideoxynucleoside.

Exemplary nucleic acid polymer carrier species are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier species comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier species includes dextran, agarose or FICOLL.

In another exemplary embodiment, the carrier species comprises a lipid (typically having 6-25 carbons), including glycolipids, phospholipids, and sphingolipids. Alternatively, the carrier species comprises a lipid vesicle, such as a liposome, or is a lipoprotein. Some lipophilic substituents are useful for facilitating transport of the conjugated dye into cells or cellular organelles.

Alternatively, the carrier species is a virus, cell, cellular system, cellular fragment, or subcellular particle, e.g., virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier species is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.*, 256: C540 (1989); and pyridyl-based and phenanthroline metal ion chelators, as described in U.S. Pat. No. 5,648,270 to Kuhn et al. (1997).

In another exemplary embodiment, the carrier species non-covalently associates with organic or inorganic materials. Exemplary embodiments of the carrier species that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

Donor and Acceptor Moieties

The fluorogenic species of the invention, when converted to the corresponding fluorescent species can be used with other light emitting or light absorbing species as components of energy transfer probes. Many appropriate species are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry*

45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

In addition to small molecule fluorophores, naturally occurring fluorescent proteins and engineered analogues of such proteins are useful with the fluorogenic species of the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from *Vibrio fischeri* strain (Baldwin et al., *Biochemistry* 29:5509-15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as *Synechococcus*, e.g., phycoerythrin and phycocyanin (Wilbanks et al., *J. Biol. Chem.* 268:1226-35 (1993)) and the like.

A non-limiting list of exemplary donors and acceptors that are of use with the compounds of the invention is provided in Table 1.

TABLE 1

Suitable moieties that can be selected as donors or acceptors in FET pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5'''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde TABLE 1-continued Suitable moieties that can be selected as donors or acceptors in FET pairs pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives The discussion that follows is generally true of the compounds of the invention in addition to the compounds known in the art discussed herein.

There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In a FET pair, it is generally preferred that an absorbance band of the acceptor substantially overlap a fluorescence emission band of the donor. When the donor (fluorophore) is a component of a probe that utilizes fluorescence resonance energy transfer (FRET), the donor fluorescent moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred fluorophores of use in conjunction with the species of the invention, include, for example, xanthene dyes, including fluoresceins, and rhodamine dyes. Many suitable forms of these compounds are widely available commercially with substituents on their phenyl moieties, which can be used as the site for bonding or as the bonding functionality for attachment to an nucleic acid. Another group of preferred fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

The fluorogens and an appropriate donor or acceptor moiety can be attached to a carrier species using any methodology known in the art. Representative methods include those relevant to preparing fluorescently labeled nucleic acids. See, for example: Eckstein, editor, Nucleic Acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink™ II available from P.E. Biosystems, Calif.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Synthesis

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

The compounds of the invention can be prepared as a single stereoisomer or as a mixture of stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

Figure 2:
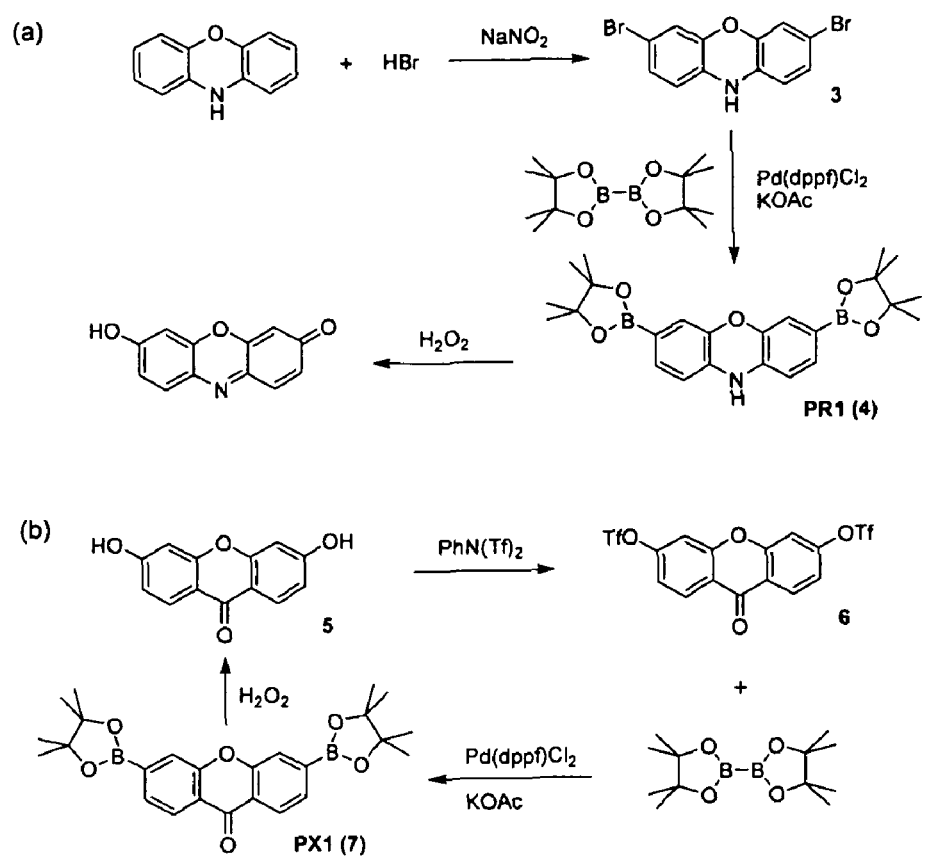
FIG. 2 is an exemplary synthetic scheme for the preparation of a probe of the invention.
Figure 3:
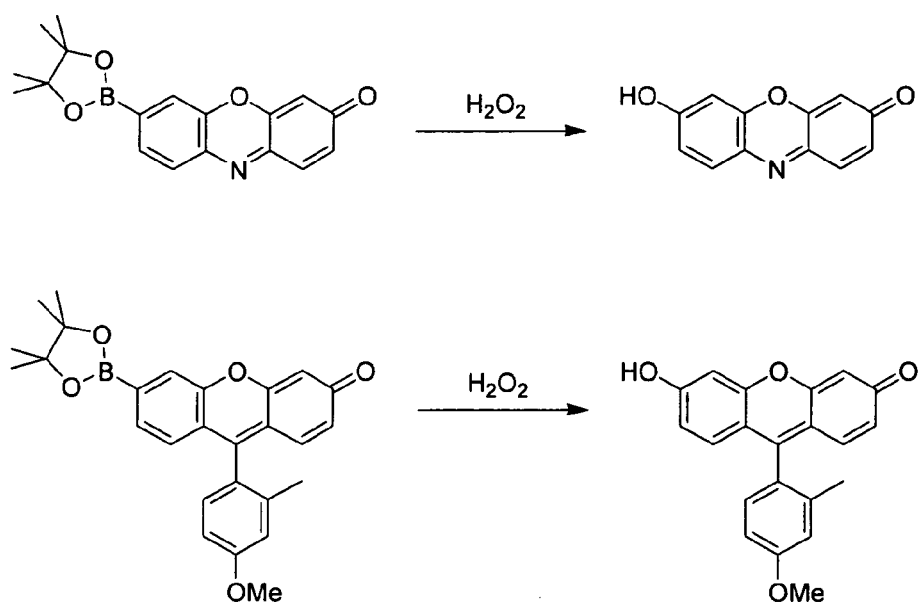
FIG. 3 is a reaction pathway showing the oxidative activation of an asymmetric probe of the invention.

Exemplary synthetic schemes leading to a probe of the invention is set forth in Scheme 1 (FIG. 1), and Scheme 2 (FIG. 2).

Scheme 1 outlines the preparation of PF1 (2). Acid-catalyzed condensation of 3-iodophenol and phthalic anhydride affords 3',6'-diiodofluoran 1. Palladium-catalyzed transmetalation of fluoran 1 under Miyaura conditions with bis(pinacolato)diboron proceeds smoothly to generate PF1 after workup and purification by column chromatography Scheme 2 outlines the syntheses of Peroxyresofurin-1 (PR1, 4) and Peroxyxanthone-1 (PX1, 7) dyes that respond to $H_2O_2$ by an increase of red and blue fluorescence, respectively. Direct bromination of phenoxazine with hydrobromic acid and sodium nitrite affords 3,7-dibromophenoxazine 3 after isolation from various other brominated products. Palladium-catalyzed transmetalation of dibromo 3 with bis(pinacolato)diboron under Miyaura conditions proceeds smoothly to generate PR1 after workup and purification by flash column chromatography. Reaction of 3,6-dihydroxyxanthone (5) with N-phenyltrifluoromethanesulfonamide in dichloromethane furnishes 3,6-di(trifluoromethanesulfonate)xanthone 6. Palladium-catalyzed transmetalation of bis-triflate 6 with bis(pinacolato)diboron delivers 7.

The above-recited synthetic schemes are intended to be exemplary of certain embodiments of the invention, those of skill in the art will recognize that many other synthetic strategies for producing the ligands of the invention are available without resort to undue experimentation.

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

Assays based on specific binding reactions are used for detecting a wide variety of substances such as drugs, hormones, enzymes, proteins, antibodies, and infectious agents in various biological fluids and tissue samples. In general, the assays consist of an analyte, a recognition moiety for the analyte, and a detectable label. Competitive assay modalities generally utilize a binding partner in addition to these components. In an exemplary embodiment, the binding partner is a molecule that interacts with a recognition moiety to form a complex that is inherently less stable than a similar complex formed between the recognition moiety and the analyte, and is subsequently displaced by the incoming analyte.

Because the results of specific binding interactions are frequently not directly observable, a variety of fluorescent labels have been devised for determining the presence of an interaction. The fluorophores of the invention are detected by use of fluorescence spectroscopy or by the naked eye. An introduction to labels, labeling procedures and detection of labels, such as are useful in practicing the present invention, is found in Polak et al., INTRODUCTION TO IMMUNOCYTOCHEMISTRY, $2^{nd}$ Ed., Springer Verlag, NY, (1977), and in Haugland, HANDBOOK OF FLUORESCENT PROBES AND RESEARCH CHEMICALS, a combined handbook and catalogue Published by Molecular Probes, Inc., Eugene, Oreg. (1996)

In certain embodiments, the assay is a competitive assay. In practice, the components of the assay (i.e., recognition moiety, binding partner and analyte) can have substantially any chemical structure, however in a preferred embodiment, the recognition moiety, the binding partner and the analyte are members independently selected from the group consisting of small molecular bioactive agents, biomolecules and combinations thereof. When a component of the assay is a biomolecule, the biomolecule is preferably a member selected from the group consisting of haptens, antibodies, antigens, carbohydrates, nucleic acids, peptides, enzymes and receptors.

In a competitive assay format, one or more than one of the components is labeled with a compound of the invention. For example, in one embodiment, the binding partner is labeled with a compound of the invention and its displacement from an immobilized recognition moiety is detected by the appearance of fluorescence in a liquid phase of the assay. In another competitive assay format, an immobilized enzyme is complexed with a substrate conjugated to a compound of the invention. The complex is then contacted with a putative antagonist. The displacement of fluorescence from the immobilized enzyme into a liquid phase of the assay is indicative of displacement of the substrate by the putative antagonist. These embodiments are offered by way of example only and it will be plain to one of skill in the art that many other competitive assay formats can utilize and benefit from the compounds of the invention.

In addition to ascertaining a binding event, it is frequently desired to quantitate the magnitude of the affinity between two or more binding partners. Thus, it is also within the scope of the present invention to utilize the compounds disclosed herein as a support for such assays.

Most typically, the amount of analyte present is measured by quantitating the amount of label fixed to a binding partner, analyte or recognition moiety following a binding event. Means of detecting and quantitating fluorescent labels are well known to those of skill in the art.

In another preferred embodiment, the affinity between two or more assay constituents is measured by quantifying a population selected from the group consisting of the analyte-recognition moiety complex, free analyte, free binding partner, binding partner-recognition moiety complex and combinations thereof.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. The binding assay can be performed, for example, in a 96-well filtration plate assembly (Millipore Corporation, Bedford, Mass.). One of the three binding partners (i.e., the ligand, antagonist or receptor) is generally bound to the well or to a particulate material contained within the well.

The assays of the invention can be practiced with some or all components in solution. Alternatively, one or more components can be substantially insoluble in the assay medium. In a preferred embodiment, one or more members selected from the group consisting of the recognition moiety, the binding partner and the analyte are attached to a surface, i.e., a solid support. Useful surfaces include, but are not limited to, glass or polymeric beads, sheets, fibers, membranes (e.g. nylon, nitrocellulose), slides (e.g. glass, quartz) and the like.

Following the displacement of the binding partner from the binding partner-recognition moiety complex, the remaining steps of the assay can be performed on the mixture that is formed by the displacement or one or more of the components of the mixture can be removed. In a preferred embodiment, the method further includes separating the free binding partner from a member of the group consisting of the recognition-binding partner pair, the analyte-recognition moiety pair and combinations thereof.

The present invention also provides methods of using the compounds described herein to detect peroxidase activity in a sample, directly or indirectly by the production of peroxide. The methods are illustrated by the use of the compound of the invention to detect an active oxygen species, e.g., $H_2O_2$. Those of skill in the art will appreciate that this focus is for clarity of illustration and does not limit the scope of the methods in which the compounds of the invention find use.

In another embodiment, the present invention provides methods of using the compounds described herein to detect an analyte in a sample, e.g., an ROS (e.g., $H_2O_2$) or as a tracing or tracking reagent in a biological sample. Alternatively, the present compounds are also used to detect or monitor production of ROS, distribution of ROS, metabolic activity in a cell including cell violability and proliferation.

In a further aspect, there is provided a method for determining the presence or absence of peroxide in a sample. The method includes: a) contacting the sample with a fluorogenic compound having a structure according to Formula I; b) incubating the labeled sample for a sufficient amount of time to allow the peroxide to react with the fluorogenic compound to produce a fluorescent product; c) illuminating the sample from b) with light of an appropriate wavelength; and d) observing the presence or absence of fluorescence from the sample, whereby the presence or absence of the peroxide in the sample is determined.

In an exemplary embodiment, the peroxide is produced by a peroxidase. The peroxidase may be an enzyme such as horseradish peroxidase or another enzyme that has peroxidase activity, but which is not generally considered a peroxidase, such as cyclooxygenase. Further exemplary enzymes of use in the methods of the invention include oxidases such as glutamate oxidase, amine oxidase, choline oxidase, cholesterol oxidase, galactose oxidase, xanthine oxidase, uricase oxidase, pyruvate oxidase, glycerin-3-phosphate oxidase, acyl Co A oxidase, glycerol oxidase and glucose oxidase.

In certain embodiments, the peroxide detected is hydrogen peroxide, such as that produced by horseradish peroxidase. In another embodiment, the peroxide is not hydrogen peroxide, but is a peroxide such as the transient peroxide produced by cyclooxygenase.

The compounds of the invention are also of use to detect the presence of an enzyme (e.g., oxidase) in a sample wherein the enzyme generates a ROS, e.g., peroxide, that is detected using a fluorogenic compound of the present invention.

In another example, a compound of the invention is utilized to detect hemoglobin in a sample.

In another example, a compound of the present invention is used to detect the activity of an acidic enzyme, e.g., phytase.

In another example, a compound of the present invention is used for the indirect detection of lipase activity. In this instance, lipase activity, in cells, breaks down triglycerides into free fatty acids and glycerol. In an exemplary assay format glycerol kinase and glycerol phosphate oxidase is added. The glycerol kinase phosphorylates the glycerol and the glycerol oxidase oxidizes the phosphorylated glycerol producing $H_2O_2$. Thus, via the addition of a compound of the invention, the peroxidase is detected, resulting in a correlation to the lipase activity of cells. This particular assay has diagnostic applications wherein the effect of drugs and diet can be accurately assessed for their affect on lipase activity, which plays a role in the degradation of unwanted triglycerides. Alternatively, an assay is designed as a more direct measure of lipase activity, wherein triglycerides are used instead of glycerol, along with triglyceride lipase.

In another embodiment, the enzyme, e.g., peroxidase, is covalently attached to a carrier species. In this instance, carrier species include, but are not limited to, an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus. In a further aspect, the carrier species is an antibody or fragment thereof, an avidin or streptavidin, a biotin, a blood component protein, a dextran, an antibody-binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, or a small-molecule drug.

In an exemplary embodiment, an enzyme, e.g., HRP, is conjugated to an anti-IgG to be used for the specific detection of a reactive protein when a compound of the present invention in used as the fluorogenic compound. This methodology can be used to detect any specific analyte in an ELISA format with either the peroxidase conjugated to secondary antibody (or other antibody-binding protein) or primary antibody.

In other embodiments, the compounds according to Formula I are utilized to stain a sample to give a detectable optical response under desired conditions by first preparing a dye solution comprising a dye compound described above, at a concentration sufficient to yield a detectable optical response under the desired conditions. Specifically the methods for staining a sample include: a) contacting the sample with a fluorogenic compound having a structure according to Formula I; b) incubating the labeled sample for a sufficient amount of time to allow reaction between the fluorogenic compound and a ROS, producing a fluorophore; c) illuminating the sample from b) with light of an appropriate wavelength to excite the fluorophore; and d) detecting fluorescence in the sample.

For example, the fluorophore derived from a fluorogenic species of the invention is used to monitor specific components of the sample with respect to their spatial and temporal distribution in the sample. Alternatively, the fluorogen or fluorophore preferentially binds to a specific analyte in a sample, enabling the researcher to determine the presence or quantity of that specific analyte. In another embodiment, the compound of the invention is used to analyze the sample for the presence of a mechanism that acts upon the fluorogen or fluorophore, e.g., oxidation or reduction. The desired analysis to be performed determines the composition of the dye solution and chemical nature of the dye itself. In another example, the fluorophore is bound by an antibody directed against the fluorophore, typically resulting in the fluorescence quenching of the fluorophore.

Figure 13:
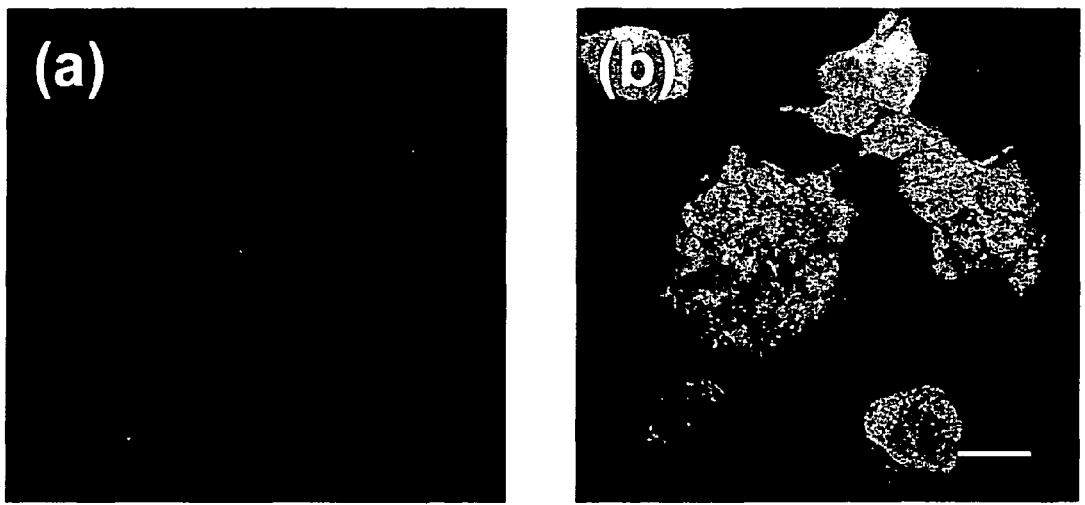
FIG. 13 shows confocal fluorescence images of live HEK cells. (a) Fluorescence image of HEK cells incubated with 5 μM PF1 for 5 min at 25° C. (b) Fluorescence image of PF1-stained HEK cells treated with 100 μM $H_2O_2$ for 11 min at 25° C. Excitation was provided at 488 nm, and emission was collected in a window from 505 to 580 nm. Scale bar=27 μm.
Figure 14:
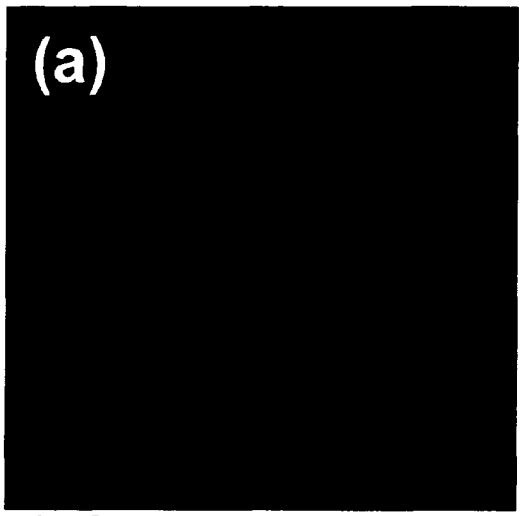
FIG. 14 shows confocal fluorescence images of live HEK cells. (a) Fluorescence image of HEK cells incubated with 10 μM PR1 for 10 min at 25° C. (b) Fluorescence image of PR1-stained HEK cells treated with 100 μM $H_2O_2$ for 30 min at 25° C. Excitation was provided at 543 nm, and emission was collected in a window from 548 to 644 nm. Scale bar=18 μm.
Figure 14:
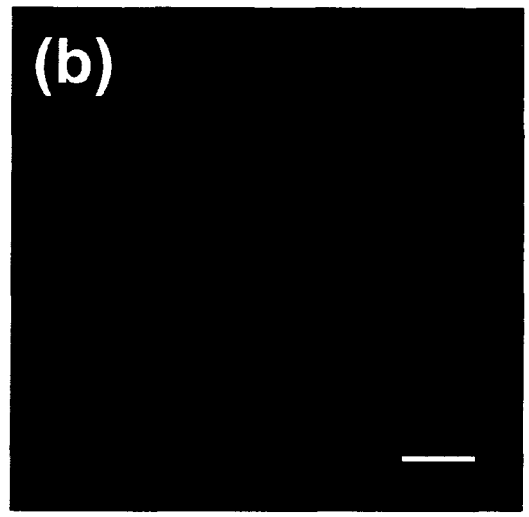
Figure 15:
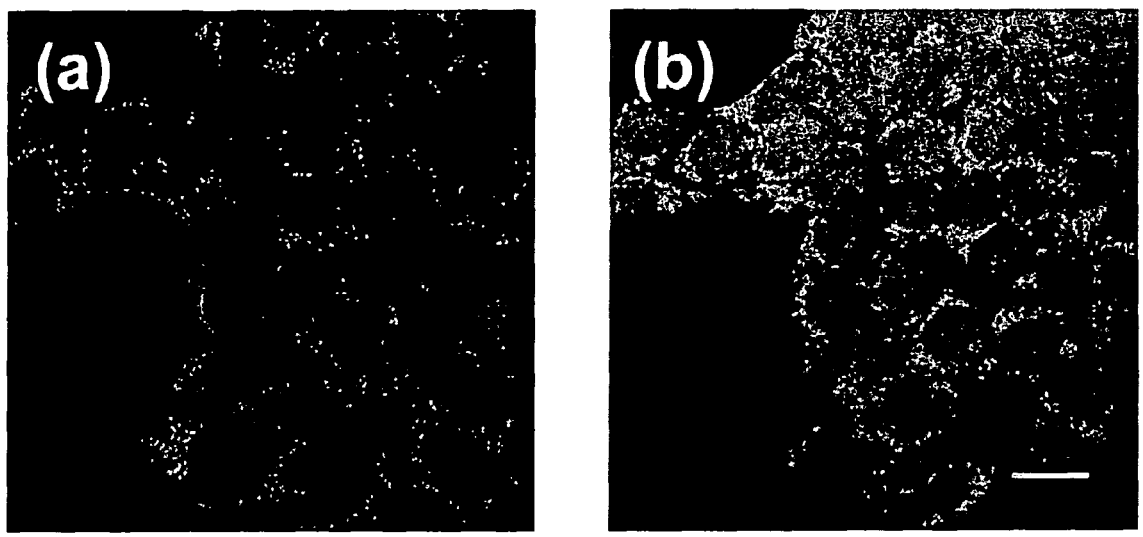
FIG. 15 shows two-photon fluorescence images of live HEK cells. (a) Fluorescence image of HEK cells incubated with 10 μM PX1 for 2-3 min at 25° C. (b) Fluorescence image of PX1-stained HEK cells treated with 100 μM $H_2O_2$ for 30 min at 25° C. Two-photon excitation was provided at 704 nm, and emission was collected in a window from 420 to 500 nm. Scale bar=18 μm

Procedures using the compounds for such applications are provided in the Examples appended hereto (FIG. 13, FIG. 14 and FIG. 15).

Optionally, the sample is washed, prior to (c), to remove residual, excess or unbound fluorogen or fluorophore. The fluorogenic probe (or its fluorescent analogue) can form a covalent or non-covalent association or complex with an element of the sample, or it is simply present within the bounds of the sample or portion of the sample. In this instance the dye may be chemically reactive, conjugated to a carrier species, or conjugated to a solid support.

For biological applications, the fluorogenic compound solution is typically an aqueous or mostly aqueous solution that comprises one or more of the compounds described herein. Solutions of the compounds of the invention are prepared according to methods generally known in the art. As with related known fluorophores and fluorogens, these compounds are generally soluble in water and aqueous solutions having a pH greater than or equal to about 6. Stock solutions of pure fluorogenic species, however, are typically dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. A labeling solution is prepared by diluting an aliquot of the stock solution into aqueous buffer to the desired labeling concentration.

In general, the amount of fluorogen or conjugate in the solution is the minimum amount required to yield detectable staining in the sample within a reasonable time, with minimal background fluorescence or undesirable staining. The exact concentration of fluorogen or conjugate to be used is dependent upon the experimental conditions and the desired results, and optimization of experimental conditions is typically required to determine the best concentration of stain to be used in a given application. The concentration of fluorogen present in the solution typically ranges from nanomolar to micromolar. The required concentration for the solution is determined by systematic variation in fluorogen or conjugate concentration until satisfactory staining is accomplished. The starting ranges are readily determined from methods known in the art for use of similar compounds under comparable conditions for the desired optical response.

The amount of reagent required for staining cells, e.g., eukaryotic cells, depends on the number of cells present, the permeability of the cell membrane to the reagent and the time required for intracellular metabolism to generate a fluorescent product. In the case of staining of tissues, the amount of reagent required may also vary with the accessibility of the reagent to the cells in the tissue. The required concentration for the labeling solution is determined by systematic variation in labeling concentration until a satisfactory fluorescent labeling is accomplished. Typically, the amount of fluorogen is selected to provide approximately 0.01 µM to about 50 µM, more typically about 0.5 µM to about 25 µM. Lower concentrations in the nanomolar range, such as from about 20 nM to about 500 nM, are typically employed when staining organelles such as mitochondria.

Low concentrations of fluorogen will typically require longer incubation times for equivalent fluorescent brightness to be reached. For example, staining mitochondria incubated in 20 nM fluorogen solution will require about 1 to 2 hours to reach an arbitrary level of fluorescent staining that is reached in about 30 minutes using a 50 nM labeling solution. Similarly, the level of staining reached in 30 minutes using a 75 nM labeling solution of a diaminodihydroxanthene dye will require incubation for 90 minutes in a 50 nM labeling solution.

In another aspect, the invention provides thiol-reactive compounds, which are of use to uniformly stain the cytoplasm of live cells. In this application the compounds are well retained in living cells through several generations. They are inherited by daughter cells after cell fusion and are not transferred to adjacent cells in a population. The cells are loaded with the present compounds by adding a solution of the compound to the culture medium and then, optionally, washing the cells briefly with fresh medium before analysis. An exemplary solution is prepared by adding a stock solution to serum-free medium at a final contraction from about 0.1 µM to about 50 µM. For cells that are rapidly proliferating or dividing the assay will generally require a higher concentration of fluorogen, typically from about 5 µM to about 50 µM, while a viability assay will typically require less fluorogen, such as from about 0.1 µM to about 10 µM. Testing of at least a ten-fold range of concentration is recommended to determine the appropriate concentration for each particular assay.

Without wishing to be bound by a theory, it is likely that the thiol-reactive compounds are probably reacting with thiols in a glutathione S-transferase-mediated reaction. In many cells, glutathione levels are high and glutathione transferase is ubiquitous. The thiol-reactive compound is transformed into a cell-impermeant fluorescent dye-thioether adduct that can be fixed with aldehyde fixatives, permitting long-term storage.

In one embodiment, the fluorogenic species of the present invention are cell permeant, and can be introduced into the sample cell or cells by incubation of the cell or cells in a solution containing the fluorogenic compound. Any other method of introducing the compound into the sample cell, such as microinjection of a solution of the fluorogen, scrape loading techniques (short mechanical disruption of the plasma membrane where the plasma membrane is peeled away from the cytoplasm, the dye is perfused through the sample and the plasma membrane reassembled), or patch clamp methods (where an opening is maintained in the plasma membrane for long periods) can be used. Any other treatment that will permeabilize the plasma membrane, such as electroporation, shock treatments or high extracellular ATP can be used to accelerate introduction of the fluorogen into the cellular cytoplasm. Microinjection of a fluorogen solution is of particular use when analysis of a single cell is desired, within a colony of other sample cells.

The sample can be observed immediately after cellular or organelle staining is evident. After staining, the cells or isolated organelles in a sample can optionally be fixed. A number of fixatives and fixation conditions are suitable for practicing this invention. Useful fixatives include, but are not limited to, formaldehyde, paraformaldehyde, formalin, glutaraldehyde, cold methanol and 3:1 methanol:acetic acid. Typically, cell fixation is accomplished by incubating in a 3.7% solution of paraformaldehyde for about 15-30 minutes.

Fixation is optionally followed or accompanied by permeabilization, such as with acetone, ethanol, DMSO or various detergents. Permeabilization is utilized to allow bulky additional detection reagents to enter the cellular space (vida infra) that would ordinarily be impermeant with respect to the cellular membrane. A large variety of fixatives, fixation conditions, and permeabilization agents are known in the art, and other methods of fixing or permeabilizing sample cells in conjunction with the stains of the present invention will be obvious to one of ordinary skill. Cells and organelles stained by dyes of the present invention retain fluorescent staining even after fixation and extensive permeabilization.

In one aspect of the invention, the fluorogen of the invention non-covalently associates with organic or inorganic materials through interaction of a substituent of the fluorogen with the material. Exemplary compounds of the invention include a lipophilic substituent can be used to stain lipid assemblies such as biological membranes or liposomes by non-covalent incorporation of the compound within the membrane, e.g. for use as probes for membrane structure or for incorporation in liposomes, lipoproteins, films, plastics, lipophilic microspheres or similar materials.

The compounds of the invention, more particularly their fluorescent analogues, are useful as coloring agents, tracers for detecting the flow of fluids such as in angiography, and tracing of fluid flow through gap junctions of neurons according to procedures known in the art for other dyes.

Fluorogens of the invention that include one or more reactive functional group can be used to label cell surfaces, cell membranes or intracellular compartments such as organelles, or in the cell's cytoplasm, Certain reactive groups allow the retention of the probe in cells or organelles by reacting with cellular materials. In particular, haloalkyl- or halomethylbenzamide-substituted fluorogens (or their fluorescent analogues) react selectively with intracellular components such as glutathione, or other groups within cells or within selected organelles where the dye compound is localized therein, according to methods previously described (U.S. Pat. No. 5,362,628 to Haugland et al, (1994); U.S. Pat. No. 5,576,424 to Mao et al. (1996) (in cells); and U.S. Pat. No. 5,459,268 to Haugland et al. (1995) and U.S. Pat. No. 5,686,261 to Zhang et al. (1997) (in mitochondria).

In another exemplary embodiment of the invention, the compounds are used to determine the efficiency of a cellular efflux pump of cells in a sample. Preferably the fluorogenic compounds are diacetates or diphosphates. The compound is preferably used in the minimum concentration that gives a detectable fluorescence emission. Once the diacetate compounds are inside the cell, the blocking acetates are cleaved and the compound becomes highly fluorescent. The efficiency of the cellular efflux pump of cells in the sample is determined by comparing the fluorescence emission of cells in the sample with the fluorescence of cells having a known efflux efficiency. Where the efflux pump is impaired, inhibited, or absent, the fluorescent compound is well retained in the cell; where the efflux pump is present and functioning, the fluorescence of the cells decreases markedly.

Multiplex Analyses

Because the compounds of the invention, which fluoresce at within a number of distinct wavelength ranges, providing fluorophores of different colors, these compounds are of use components of one or more probes used in an assay designed to detect multiple species in a sample. An assay used to detect two or more species by using at least two probes bearing different fluorophores is referred to herein as a "multiplex analysis."

Probes that include the compounds of the invention are also useful in performing multiplex-type analyses and assays. In a typical multiplex analysis, two or more distinct species (or regions of one or more species) are detected using two or more probes, wherein each of the probes is labeled with a different fluorogen of the invention. Preferred multiplex analyses relying on fluorescent energy transfer ideally meet several criteria. The fluorescent species should be bright and spectrally well-resolved and the energy transfer between the fluorescent species and the acceptor should be efficient.

The fluorogenic species of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., Salmonella), nucleic acids (e.g., DNA, RNA, and analogues thereof), polysaccharides, lipopolysaccharides, lipids, fatty acids, non-biological polymers and small bioactive molecules (e.g., toxins, drugs, pesticides, metabolites, hormones, alkaloids, steroids).

Sample Preparation

The end user will determine the choice of the sample and the way in which the sample is prepared. The sample includes, without limitation, any biological derived material or aqueous solution that is thought to contain a target analyte, peroxide or an enzymatic system that produces peroxide. The samples may also include a reactive oxygen species, e.g., peroxide, or a molecule or system, e.g., an enzymatic system that produces peroxide. Furthermore, the sample can include a buffer solution that contains a peroxidase, peroxide and fluorogenic compounds of the present invention to determine the ability of the sample to oxidize the compound of the invention.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, .beta. cells, hepatocytes, and neurons.

Various buffers may be used that do not interfere with the generation of a fluorescent signal by conversion of the fluorogen. These buffers include PBS, Tris, MOPS, HEPES, phosphate, etc. The pH will vary depending upon the particular monooxygenase being assayed, generally being in the range of about 7.0-7.5, where the pH is selected to provide for at least about maximum enzyme activity. The concentration of buffer will be sufficient to prevent a significant change in pH during the course of the reaction, generally being in the range of about 0.1 to 100 mM, more usually 0.5 to 50 mM.

The reaction time will usually be at least about 5 min, more usually at least about 30 min and preferably not more than about 120 min, depending upon the temperature, concentrations of enzyme and substrate, etc. By using a specific time period for the reaction or measuring the fluorescence at 2 different times, the rate of reaction can be determined for comparison with other determinations. The temperature will generally be in the range of about 20 to 50° C., more usually in the range of about 25 to 40° C.

In certain instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

After sufficient time for a detectable amount of product to form, the reaction is optionally quenched. Various quenching agents may be used, both physical and chemical. Conveniently, a small amount of a water-soluble inhibitor may be added, such as acetonitrile, DMSO, SDS, methanol, DMF, etc. The amount of inhibitor will vary with the nature of the inhibitor and may be determined empirically.

Kits

In another aspect, the present invention provides kits that include a fluorogenic or fluorescent compound of the invention. The kit will generally also include instructions for using the compound of the invention in one or more methods.

In an exemplary embodiment, the kit includes a reactive compound of the invention and instructions for conjugating the fluorogen to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g., proteins, oligonucleotides or carbohydrates), polymeric resins and plastics (e.g., polystyrene), metals, glasses, and other organic or inorganic substances. The fluorogens of the present invention are well-suited for the preparation of such a kit.

In another exemplary kit of the invention, the instructions provided are for performing an assay that detects oxidative or reductive agents or conditions in a sample. For example, in one embodiment, directions are provided for detecting a reactive oxygen species, or an enzyme, organism, or other agent that generates a reactive oxygen species in a sample. In one aspect the kit further comprises an enzyme, a catalyst, a reaction buffer, an enzyme substrate, a peroxide, a stop solution, or a positive control. In one aspect the enzyme has oxidase or peroxidase activity.

In another exemplary kit of the invention, the instructions provided are for performing an ELISA wherein a peroxidase is conjugated to a carrier species, and a compound according to Formula I is provided as the fluorogenic substrate. In an exemplary embodiment the peroxidase is HRP. In one aspect the carrier species is an amino acid, a peptide, a protein, a polysaccharide, a nucleoside, a nucleotide, an oligonucleotide, a nucleic acid polymer, a hapten, a biotin-binding protein, a psoralen, a drug, a hormone, a lipid, a lipid assembly, a synthetic polymer, a polymeric microparticle, a biological cell or a virus. In a further aspect, the carrier species is an antibody or fragment thereof, an avidin or streptavidin, a biotin, a blood component protein, a dextran, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide. In another aspect the carrier species specifically associates with the analyte, such as a primary antibody the binds the target analyte. Alternatively, the carrier species binds to the primary antibody, such as anti-IgG, anti-IgE or anti-IgA.

Microarrays

The invention also provides microarrays including immobilized fluorogenic species and compounds functionalized with fluorogenic species. Moreover, the invention provides methods of interrogating microarrays using probes that are functionalized with fluorogenic species. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of fluorogenic species in conjunction with nucleic acid microarrays. This focus is intended to be illustrative and does not limit the scope of materials with which this aspect of the present invention can be practiced.

Thus, in another preferred embodiment, the compounds of the present invention are utilized in a microarray format. The fluorogenic species, or species bearing fluorogenic species can themselves be components of a microarray or, alternatively they can be utilized as a tool to screen components of a microarray.

Thus, in a preferred embodiment, the present invention provides a method of screening a microarray. The method includes contacting the members of the microarray with a fluorogenic species-bearing probe and interrogating the microarray for regions of fluorescence. The fluorescent regions are indicative of the presence of an interaction between the fluorogenic species-bearing probe and a microarray component. In another version of this method, the microarray is interrogated for regions in which fluorescence is quenched, again indicating the presence of an interaction between the fluorogenic species-bearing probe and a component of the microarray.

In a further preferred embodiment, the microarrays comprise n probes that comprise identical or different nucleic acid sequences. Alternatively, the microarray can comprise a mixture of n probes comprising groups of identical and different nucleic acid sequences identical nucleic acid sequences). In a preferred embodiment, n is a number from 2 to 100, more preferably, from 10 to 1,000, and more preferably from 100 to 10,000. In a still further preferred embodiment, the n probes are patterned on a substrate as n distinct locations in a manner that allows the identity of each of the n locations to be ascertained.

In yet another preferred embodiment, the invention also provides a method for preparing a microarray of n fluorogenic species-bearing probes. The method includes attaching fluorogenic species-bearing probes to selected regions of a substrate. A variety of methods are currently available for making arrays of biological macromolecules, such as arrays nucleic acid molecules. The following discussion focuses on the assembly of a microarray of fluorogenic species-bearing probes, this focus is for reasons of brevity and is intended to be illustrative and not limiting.

One method for making ordered arrays of fluorogenic species-bearing probes on a substrate is a "dot blot" approach. In this method, a vacuum manifold transfers a plurality, e.g., 96, aqueous samples of probes from 3 millimeter diameter wells to a substrate. The probe is immobilized on the porous membrane by baking the membrane or exposing it to UV radiation. A common variant of this procedure is a "slot-blot" method in which the wells have highly-elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990).

An alternate method of creating ordered arrays of probes is analogous to that described by Pirrung et al. (U.S. Pat. No. 5,143,854, issued 1992), and also by Fodor et al., (*Science,* 251: 767-773 (1991)). This method involves synthesizing different probes at different discrete regions of a particle or other substrate. This method is preferably used with relatively short probe molecules, e.g., less than 20 bases. A related method has been described by Southern et al. (*Genomics,* 13: 1008-1017 (1992)).

Khrapko, et al., *DNA Sequence,* 1: 375-388 (1991) describes a method of making an nucleic acid matrix by spotting DNA onto a thin layer of polyacrylamide. The spotting is done manually with a micropipette.

The substrate can also be patterned using techniques such as photolithography (Kleinfield et al., *J. Neurosci.* 8:4098-120 (1998)), photoetching, chemical etching and microcontact printing (Kumar et al., *Langmuir* 10:1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., *J. Am. Chem. Soc.* 117:3274-75 (1995). Similarly, using photolithography, patterns with features as small as 1 µm are produced. See, Hickman et al., *J. Vac. Sci. Technol.* 12:607-16 (1994). Patterns which are useful in the present invention include those which include features such as wells, enclosures, partitions, recesses, inlets, outlets, channels, troughs, diffraction gratings and the like.

The following examples are offered to illustrate selected embodiments of the invention and not to define or limit the scope of the present invention.

EXAMPLES

Example 1

Synthetic Materials and Methods

Silica gel 60 (230-400 mesh, Fisher) was used for column chromatography. Analytical thin layer chromatography was performed using Fisher 60 F254 silica gel (precoated sheets, 0.25 mm thick). Dichloro[1,1'-bis(diphenylphosphino)ferrocene]palladium (II), Pd(dppf)Cl$_2$, and 1,1'-bis(diphenylphosphino)ferrocene, dppf, were purchased from Strem Chemicals (Newburyport, Mass.), anhydrous DMF and anhydrous 1,4-dioxane were purchased from Acros Organics (Morris Plains, N.J.), and these reagents were used as received. All other chemicals were purchased from Sigma-Aldrich (St. Louis, Mo.) and were used as received. Tetrahydrofuran was dried and distilled over sodium/benzophenone using standard methods. 3',6'-Bis(pinacolatoboron)fluoran (Peroxyfluor-1, PF1, 1) was prepared as described previously and 3,6-dihydroxyxanthone 4 was synthesized according to a literature method. $^1$H NMR and $^{19}$F NMR spectra were collected in CDCl$_3$, CD$_3$OD, d$^6$-DMSO, or d$^6$-acetone (Cambridge Isotope Laboratories, Cambridge, Mass.) at 25° C. using either a Bruker AV-300, Bruker AVQ-400, or Bruker AVB-400 spectrometer at the College of Chemistry NMR Facility at the University of California, Berkeley. All chemical shifts are reported in the standard δ notation of parts per million. High-resolution mass spectral analyses were carried out at the College of Chemistry Mass Spectrometry Facility at the University of California, Berkeley.

1.1 Synthesis of 3',6'-Diiodofluoran (1)

3-Iodophenol (5.5 g, 25 mmol), phthalic anhydride (1.9 g, 12.5 mmol), and methanesulfonic acid (12.5 mL) were added to a 75-mL heavy-walled reaction flask and heated at 135° C. for 48 h. After cooling to room temperature, the dark purple solution was poured into 600 mL of an ice/water slurry and stirred to precipitate a grey solid. The solid was collected by filtration and dissolved in chloroform before passing through a plug of silica to yield a pink solution. The solution was evaporated to dryness and the resulting pale orange solid was recrystallized from dichloromethane to give fluoran 1 a white solid (1.7 g, 25% yield). $^1$H NMR (CDCl$_3$, 300 MHz): δ 8.04 (1H, dd, $J_1$=6.6 Hz, $J_2$=2.4 Hz), 8.04 (2H, dd, $J_1$=6.6 Hz, $J_2$=2.4 Hz), 7.70 (2H, d, J=1.8 Hz), 7.67 (2H, m), 7.39 (2H, dd, $J_1$=8.4 Hz, $J_2$=1.8 Hz), 7.13 (1H, dd, $J_1$=6.0 Hz, $J_2$=1.5 Hz), 6.55 (1H, d, J=8.4 Hz). HRFAB-MS: calculated for [MH$^+$] 552.8798. found 552.8807.

1.2 Synthesis of 3',6'-Bis(pinacolatoboron)fluoran (Peroxyfluor-1, PF1 (2))

Fluoran 1 (60 mg, 0.11 mmol), bis(pinacolato) diboron (83 mg, 0.33 mmol), potassium acetate (64 mg, 0.65 mg), and Pd(dppf)Cl$_2$ (8 mg, 0.011 mmol) were dried in vacuo in a 50-mL Schlenk flask before adding anhydrous DMF (5 mL) by syringe. The reaction was heated at 80° C. for 2 h under nitrogen. The dark brown reaction was cooled to room temperature and poured into 50 mL of water. The solid was collected by filtration, redissolved in dichloromethane, and evaporated to dryness. Purification by flash chromatography (silica gel, 1% methanol/dichloromethane) yielded diboronic ester 2 as a white solid (30 mg, 50% yield). $^1$H NMR (CDCl$_3$, 300 MHz): δ 8.04 (1H, t, J=3.9 Hz), 7.74 (2H, s), 7.61 (2H, t, J=3.9 Hz), 7.44 (2H, dd, $J_1$=7.8 Hz, $J_2$=0.9 Hz), 7.08 (1H, t, J=3.9 Hz), 6.87 (2H, d, J=7.8 Hz), 1.36 (24H, s). HRFAB-MS: calculated for [MH$^+$] 553.2569. found 553.2579.

1.3 Synthesis of 3,7-Dibromophenoxazine (3)

Concentrated hydrobromic acid (48% in water, 30 mL) was added to a solution of phenoxazine (2.01 g, 11 mmol) in acetone (17.5 mL) and the resulting purple-colored reaction mixture was stirred at room temperature for 15 min. A saturated aqueous solution of sodium nitrite (2.02 g, 29 mmol) was added dropwise to the mixture over a period of 3 min, and the reaction was stirred at room temperature for an additional 15 min. The resulting precipitate was filtered off, washed with water (200 mL), and redissolved in hot acetone (200 mL). The acetone was removed by rotary evaporation to leave a dark purple residue, which was purified by flash column chromatography (silica gel, 3:1 hexanes/ethyl acetate) to afford dibromo 3 as a metallic blue solid (375 mg, 10% yield). $^1$H NMR (d$^6$-acetone, 300 MHz): δ 6.90 (2H, dd, $J_1$=8.1 Hz, $J_2$=2.1 Hz), 6.79 (2H, s), 6.46 (2H, d, J=8.4 Hz). HRFAB-MS: calculated for [M$^+$] 338.889. found 338.889.

1.4 Synthesis of 3,7-Bis(pinacolatoboron)phenoxazine (Peroxyresorufin-1, PR1 (4))

Dibromo 3 (202 mg, 0.59 mmol), bis(pinacolato)diboron (465 mg, 1.83 mmol), potassium acetate (362 mg, 3.68 mmol), and Pd(dppf)Cl$_2$ (52 mg, 0.064 mmol) were dried in vacuo in a 50-mL Schlenk flask before adding anhydrous DMF (6 mL) by syringe. The reaction was heated at 80° C. for 2 h under nitrogen. After cooling to room temperature, the dark brown solution was added to 600 mL of ice water. The resulting light-brown precipitate was collected by filtration, redissolved in dichloromethane, and evaporated to dryness. Purification by flash column chromatography (silica gel, 5% methanol/dichloromethane) delivered diboronic ester 4 as a red-orange solid (178 mg, 69% yield). $^1$H NMR (d$^6$-acetone, 300 MHz): δ 7.12 (2H, d, J=6.3 Hz), 6.92 (2H, s), 6.49 (2H, d, J=7.5 Hz), 1.30 (24H, s). HRFAB-MS: calculated for [M$^+$] 435.238. found 435.238.

1.5 Synthesis of 3,6-Bis(trifluoromethanesulfonyl)xanthone (6)

3,6-DIHYDROXYXANTHONE (63 MG, 0.28 MMOL) AND N-PHENYLTRIFLUOROMETHANESULFONIMIDE (200 MG, 0.56 MMOL) WERE DISSOLVED IN 4 ML OF ANHYDROUS THF. N,N-DIISOPROPYLETHYLAMINE (HÜNIG'S BASE, 0.12 ML, 0.69 MMOL) WAS ADDED VIA SYRINGE, AND THE RESULTING SOLUTION WAS STIRRED AT ROOM TEMPERATURE OVERNIGHT. THE REACTION WAS TAKEN TO DRYNESS BY ROTARY EVAPORATION AND PURIFICATION BY FLASH COLUMN CHROMATOGRAPHY (SILICA GEL, 5% METHANOL/DICHLOROMETHANE) GAVE BIS-TRIFLATE 6 AS A WHITE POWDER (116 MG, 85% YIELD). $^1$H NMR (CDCL$_3$, 400 MHZ): Δ 8.44 (1H, D, J=8.8 HZ), 7.49 (1H, S), 7.35 (1H, D, J=8.8 HZ). $^{19}$F NMR (CDCL$_3$, 376 MHZ): Δ-71.76 (S). HRFAB-MS: CALCULATED FOR [MH$^+$] 492.949. FOUND 492.949.

1.6 Synthesis of 3,6-Bis(pinacolatoboron)xanthone (Peroxyxanthone-1, PX1, (7))

In an inert atmosphere glovebox, bis-triflate 6 (200 mg, 0.41 mmol), bis(pinacolato) diboron (226 mg, 0.89 mmol), Pd(dppf)Cl$_2$.CH$_2$Cl$_2$, (23 mg, 0.028 mmol), dppf (16 mg, 0.028 mmol), potassium acetate (120 mg, 1.22 mmol), and anhydrous 1,4-dioxane (6 mL) were combined in a 25-mL Schlenk flask. The vessel was removed from the glovebox and stirred at 100° C. for 12 h under nitrogen. The reaction was then cooled to room temperature, diluted with toluene, and washed three times with brine. The organic layer was dried over Na$_2$SO$_4$ and the solvent was removed by rotary evaporation to leave a brown residue. The residue was washed with methanol to furnish pure boronate 7 as a white powder (94 mg, 51% yield). $^1$H NMR (CDCl$_3$, 300 MHz): δ 8.31 (1H, d, J=7.8 Hz), 7.93 (1H, s), 7.16 (1H, d, J=7.8 Hz). HRFAB-MS: calculated for [MH$^+$] 449.231. found 449.232.

Example 2

Spectroscopic Materials and Methods

Millipore water was used to prepare all aqueous solutions. All spectroscopic measurements were performed in 20 mM HEPES buffer, pH 7. Absorption spectra were recorded using a Varian Cary 50 spectrophotometer (Walnut Creek, Calif.). Fluorescence spectra were recorded using a Photon Technology International Quanta Master 4 L-format scanning spectrofluorometer (Lawrenceville, N.J.) equipped with an LPS-220B 75-W xenon lamp and power supply, A-1010B lamp housing with integrated igniter, switchable 814 photon-counting/analog photomultiplier detection unit, and MD5020 motor driver. Samples for absorption and fluorescence measurements were contained in 1-cm×1-cm quartz cuvettes (1.4- or 3.5-mL volume, Starna, Atascadero, Calif.).

2.1 Preparation and Staining of Cell Cultures

HEK 293T cells were cultured in Dulbecco's Modified Eagle Medium (DMEM, Invitrogen, Carlsbad, Calif.) supplemented with 10% Fetal Bovine Serum (FBS, Invitrogen), glutamine (2 mM), and penicillin/streptomycin (50 µg/ml, Invitrogen). One day before imaging, cells were passed and plated on 18-mm glass coverslips coated with poly-L-lysine (50 µg/ml, Sigma, St. Louis, Mo.). Immediately before the experiments, cells were washed with PBS buffer, incubated with the probe in PBS, and imaged.

Hippocampal primary cultures were prepared from embryonic day 18 (E18) rat embryos according to a previously reported protocol. Briefly, hippocampi were dissociated by treatment with trypsin for 20 min at 37° C. followed by washing. The neuronal cells were plated on glass coverslips (Carolina Biological, Burlington, N.C.) coated with poly-L-lysine (50 µg/ml, Sigma) and cultured in neurobasal medium supplemented with 2 mM Glutamax and 2% B-27 (Invitrogen). After 10 days in vitro, the cultures were washed with PBS, incubated with the probe in PBS, and imaged.

2.2 Fluorescence Imaging Experiments

Confocal fluorescence imaging was performed with a Zeiss LSM510 META laser scanning microscope containing an Axioplan 2 MOT upright microscope and a 40× water-immersion objective lens. Excitation of PF1-loaded cells at 488 nm was carried out with an argon ion laser, and emission was collected in a window from 505 nm to 580 nm using a META detection system. Excitation of PR1-loaded cells at 543 nm was carried out with a HeNe laser, and emission was collected in a window from 548 nm to 644 nm using a META detector. PF1 or PR1 were incubated with live cell samples for 5 to 10 min. Addition of $H_2O_2$ (10 to 100 µM) to cell samples was performed directly on the microscope stage by bath application to the media.

Two-photon fluorescence imaging of PX1 was carried out using an inverted Zeiss LSM510 Axiovert 200M microscope with a NeoFLUAR 40×/1.3 NA oil-immersion objective lens. Samples were excited by 704-nm pulses from a mode-locked Ti:Sapphire laser (Tsunami, SpectraPhysics, 120-150 fs pulse width, 80 MHz repetition rate). The emission light was filtered with a 80-nm wide bandpass filter centered at 460 nm (460BP40, Chroma) and detected with the non-descanned detector (NDD) of the LSM510.

2.3 Spectroscopic Properties and Optical Responses to $H_2O_2$

Figure 4:
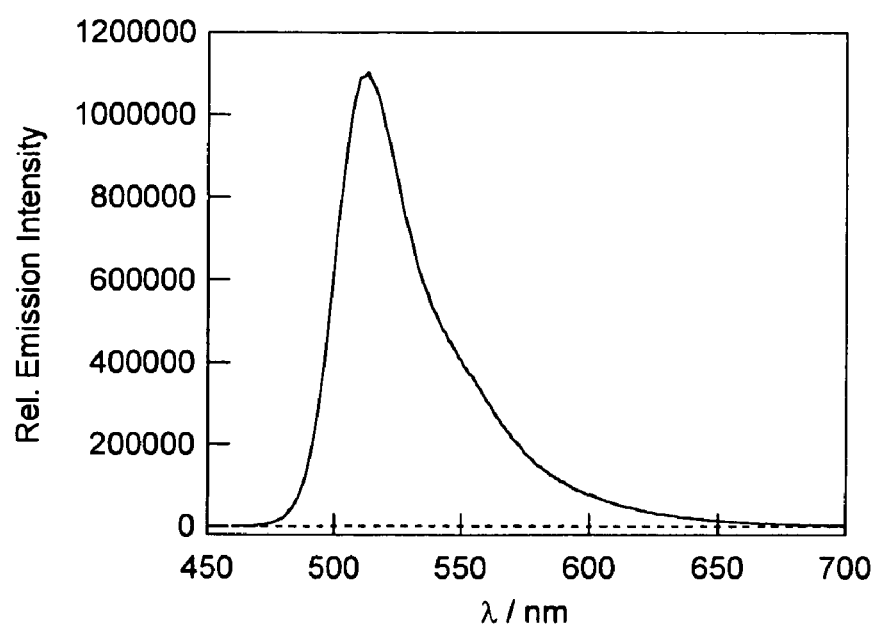
FIG. 4 is the fluorescence response of 5 μM PF1 (2) to 100 μM $H_2O_2$. The dotted and solid line spectra were recorded before and after $H_2O_2$ addition, respectively. Spectra were acquired in 20 mM HEPES, pH 7 ($\lambda_{exc}$=450 nm).
Figure 5:
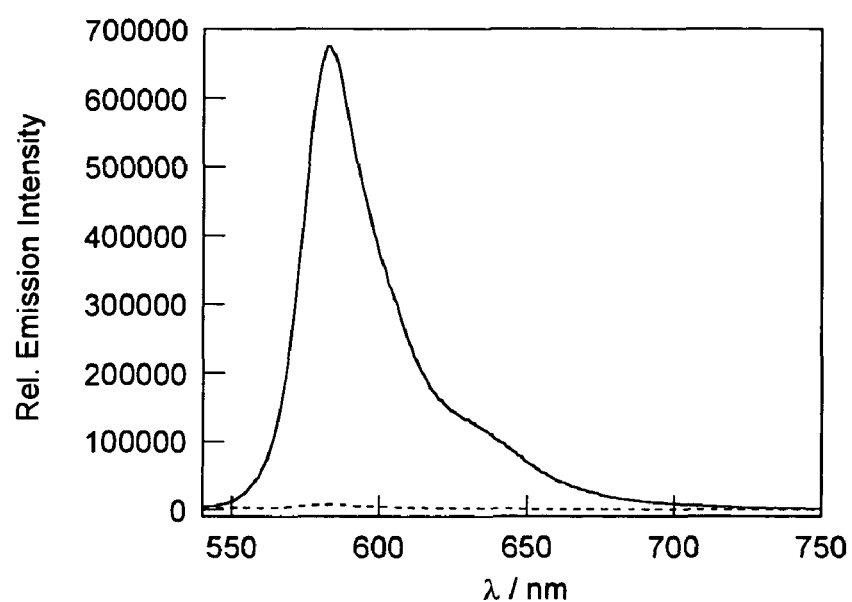
FIG. 5 is the fluorescence response of 5 μM PR1(4) to 100 μM $H_2O_2$. The dotted and solid line spectra were recorded before and after $H_2O_2$ addition, respectively. Spectra were acquired in 20 mM HEPES, pH 7 ($\lambda_{exc}$=530 nm).
Figure 6:
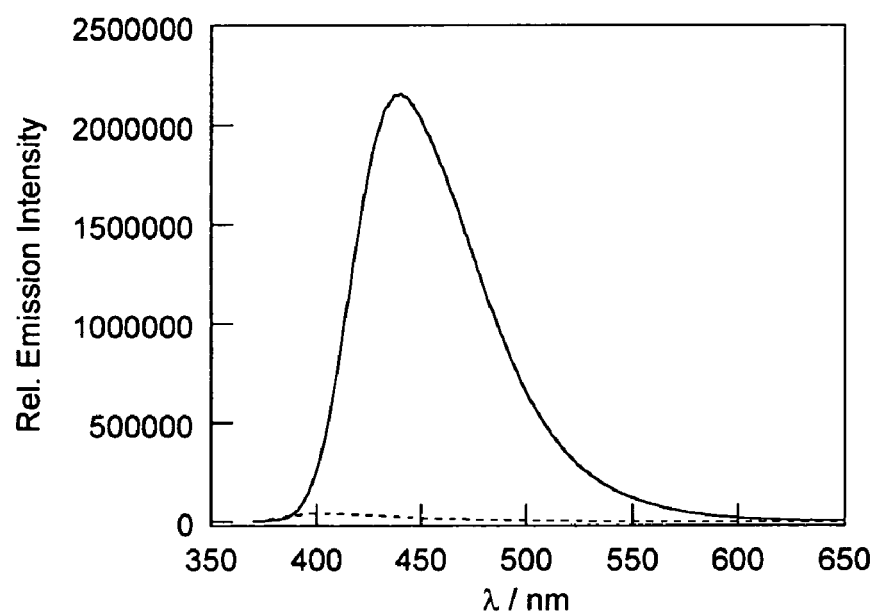
FIG. 6 is the fluorescence response of 20 μM PX1 (7) to 100 μM $H_2O_2$. The dotted and solid line spectra were recorded before and after $H_2O_2$ addition, respectively. Spectra were acquired in 20 mM HEPES, pH 7 ($\lambda_{exc}$=350 nm).

The Peroxysensor reagents were evaluated under simulated physiological conditions (20 mM HEPES buffer, pH 7). As expected, PF1 and PR1 are non-fluorescent and display no absorption features in the visible region. PX1 has an ultraviolet absorption maximum centered at 350 nm ($\epsilon=4.7\times10^3$ $M^{-1}$ $cm^{-1}$) and exhibits weak fluorescence with an emission maximum at 400 nm. The addition of $H_2O_2$ triggers prompt increases in fluorescence for all three probes. FIG. 4, FIG. 5 and FIG. 6 show the fluorescence responses of PF1, PR1, and PX1, respectively, to $H_2O_2$. For PF1 and PR1, the fluorescence increases induced by $H_2O_2$ occur with concomitant growth of visible wavelength absorption bands characteristic of green-fluorescent fluorescein and red-fluorescent resorufin, respectively. Absorption and emission spectra, along with electrospray ionization mass spectrometry, establish that fluorescein is the product generated from the reaction between PF1 and $H_2O_2$ (FIG. 1) and resorufin is the product afforded from the reaction between PR1 and $H_2O_2$ (FIG. 2a). Analogous experiments with PX1 show that its reaction with $H_2O_2$ produces blue-fluorescent 3,6-dihydroxyxanthone, with a 52-fold increase in integrated fluorescence intensity and a concomitant shift in emission maximum from 400 to 450 nm (FIG. 2b). The dynamic ranges of PF1 and PR1 are even larger (>1000-fold increase in integrated emission), owing to their binary absorption/emission response. These values represent a 5- to 500-fold improvement in $H_2O_2$ dynamic range compared to previously reported probes. For comparison, $H_2O_2$ probes based on sulfonate deprotection have a dynamic range of up to 2.5, lanthanide complexes display increases of up to 15-fold upon $H_2O_2$ addition, and phosphine-containing fluorophores for non-specific detection of hydroperoxides in water show an on-off ratio of up to 78 (higher values are obtained in 1:1 organic:aqueous solution). Dihydro derivatives of fluorescein and rhodamine dyes show comparable dynamic ranges to the Peroxysensor family in response to $H_2O_2$, but are not nearly as selective for $H_2O_2$ over other ROS (vide infra). For example, DCFH shows a 190-fold increase upon addition of $H_2O_2$ but increases by ca. 7000-fold by reaction with .OH or peroxynitrite ($ONOO^-$), 150-fold with NO, 67-fold with $O_2^-$, and 2000-fold upon light-induced autoxidation.

Figure 7:
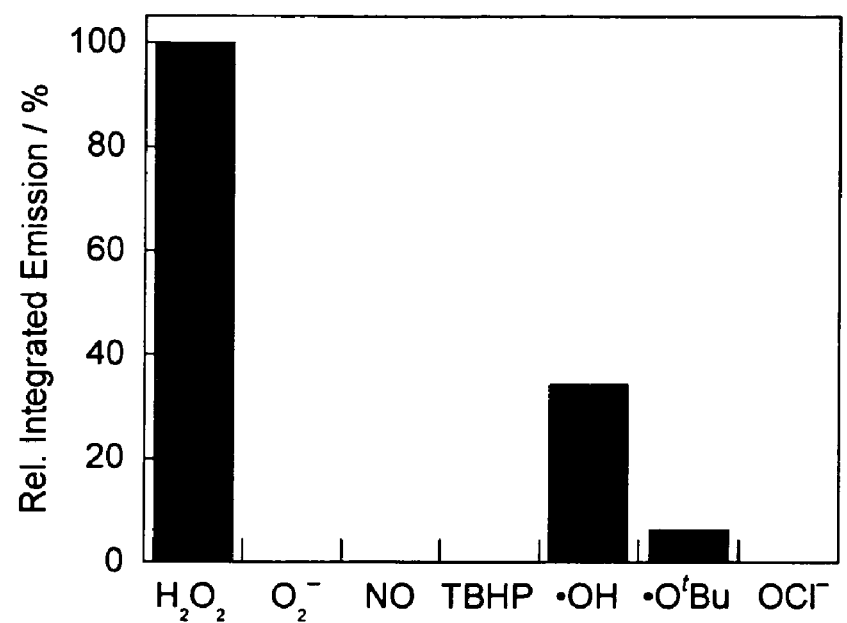
FIG. 7 is the fluorescence response of 5 μM PF1 to various ROS (10 mM $O_2^-$, 100 μM for all other ROS). .OH and .Ot-Bu were generated by reaction of $Fe^{2+}$ with $H_2O_2$ or tert-butyl hydroperoxide (TBHP), respectively. NO was delivered using S-nitrosocysteine (SNOC). Spectra were acquired in 20 mM HEPES, pH 7, and all data were obtained after incubation with the appropriate ROS at 25° C. for 1 h. Collected emission was integrated between 460 and 700 nm ($\lambda_{exc}$=450 nm).
Figure 8:
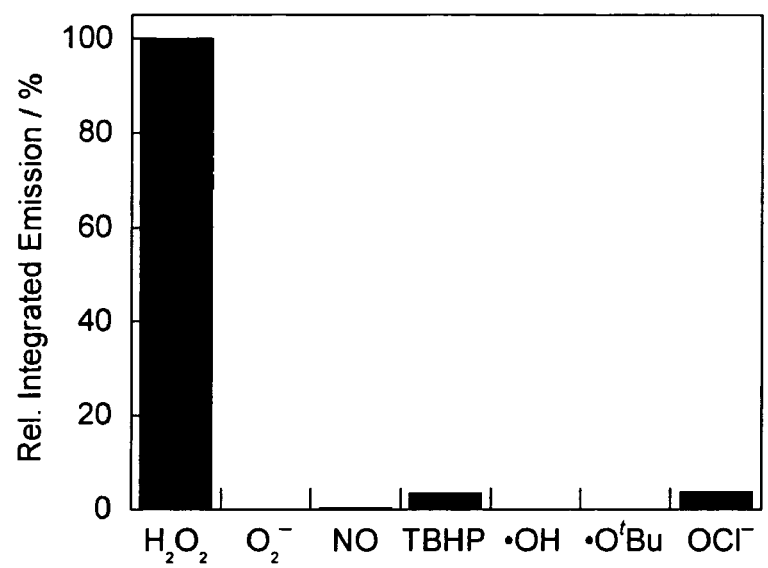
FIG. 8 is the fluorescence response of 5 μM PR1 to various ROS (10 mM $O_2^-$, 100 μM for all other ROS). .OH and .O$^t$Bu were generated by reaction of $Fe^{2+}$ with $H_2O_2$ or tert-butyl hydroperoxide (TBHP), respectively. NO was delivered using S-nitrosocysteine (SNOC). Spectra were acquired in 20 mM HEPES, pH 7, and all data were obtained after incubation with the appropriate ROS at 25° C. for 30 min. Collected emission was integrated between 570 and 800 nm ($\lambda_{exc}$=560 nm).
Figure 9:
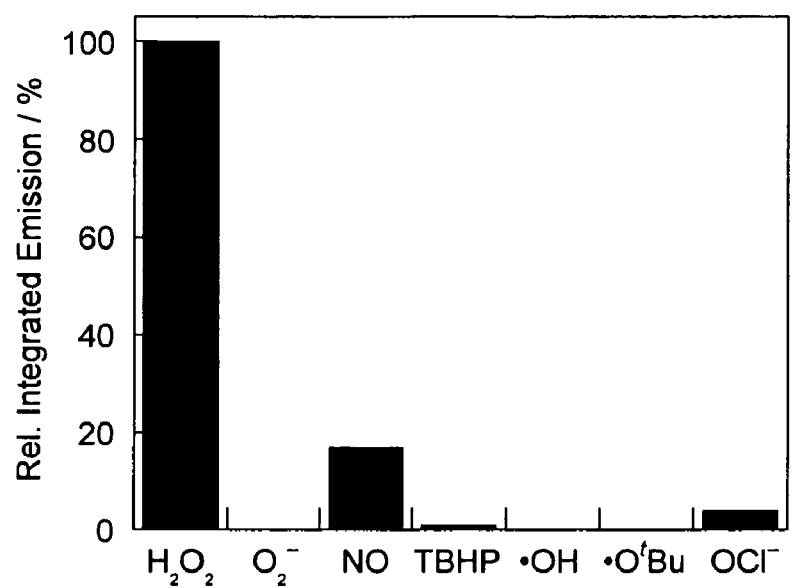
FIG. 9 is the fluorescence response of 10 μM PX1 to various ROS (10 mM $O_2^-$, 100 μM for all other ROS). .OH and .Ot-Bu were generated by reaction of $Fe^{2+}$ with $H_2O_2$ or tert-butyl hydroperoxide (TBHP), respectively. NO was delivered using S-nitrosocysteine (SNOC). Spectra were acquired in 20 mM HEPES, pH 7, and all data were obtained after incubation with the appropriate ROS at 25° C. for 1 h. Collected emission was integrated between 370 and 600 nm ($\lambda_{exc}$=350 nm).

The fluorescence responses of the Peroxysensor platforms are highly $H_2O_2$ selective. FIG. 7, FIG. 8 and FIG. 9 compare the relative reactivities of boronate-based PF1, PR1, and PX1, respectively, toward various ROS. PF1 exhibits a >500-fold higher response for $H_2O_2$ over similar ROS such as $O_2^-$, NO, tert-butyl hydroperoxide (TBHP), or $^-OCl$ (FIG. 4). The green-fluorescent xanthenone probe also displays selectivity for $H_2O_2$ over highly oxidizing ROS such as .OH (>3-fold higher for $H_2O_2$) and .O$^t$Bu (>15-fold higher for $H_2O_2$). PR1 is >1000 times more responsive to $H_2O_2$ than $O_2^-$ and shows a >200-fold higher response for $H_2O_2$ over NO and reactive radicals .OH and .O$^t$Bu (FIG. 5). This red-fluorescent reagent is also >25-fold more selective for $H_2O_2$ over either TBHP or $^-OCl$. PX1 also shows notable discrimination for $H_2O_2$ over other ROS (FIG. 6). This blue-fluorescent reporter shows a >500-fold higher response for $H_2O_2$ over $O_2^-$ and the oxygen radicals .OH and .O$^t$Bu and is >100-fold more reactive toward $H_2O_2$ over TBHP. PX1 is also >25-fold more selective for $H_2O_2$ over $^-OCl$ and ca. 6-fold more responsive to $H_2O_2$ over NO. The values measured for the Peroxysensor platforms represent a 10- to 100-fold improvement in $H_2O_2$ selectivity compared to previously reported probes, establishing that chemoselective boronate deprotection provides a general and effective mechanism for detecting $H_2O_2$ selectively over other more oxidizing ROS.

Figure 10:
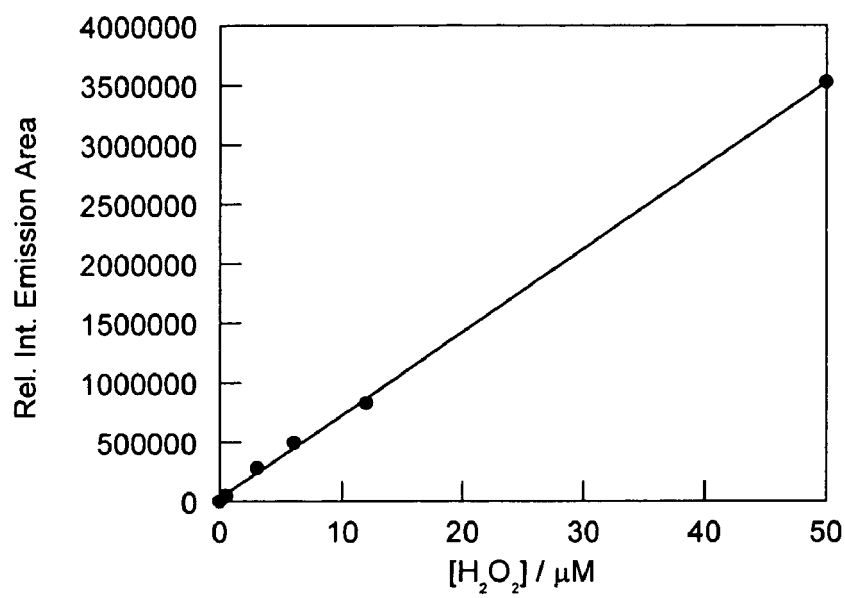
FIG. 10 is the fluorescence responses of 5 μM PF1 to various concentrations of $H_2O_2$. Spectra were acquired in 20 mM HEPES, pH 7, and all data were obtained after incubation with $H_2O_2$ at 25° C. for 15 min. Collected emission was integrated between 460 and 700 nm ($\lambda_{exc}$=450 nm).
Figure 11:
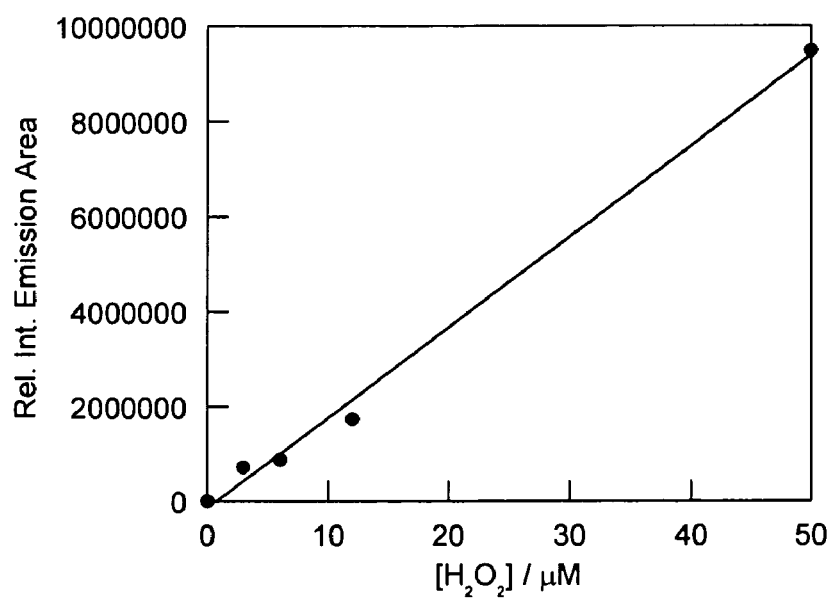
FIG. 11 is the fluorescence response of 5 μM PR1 to various concentrations of $H_2O_2$. Spectra were acquired in 20 mM HEPES, pH 7, and all data were obtained after incubation with $H_2O_2$ at 25° C. for 15 min. Collected emission was integrated between 560 and 800 nm ($\lambda_{exc}$=550 nm).
Figure 12:
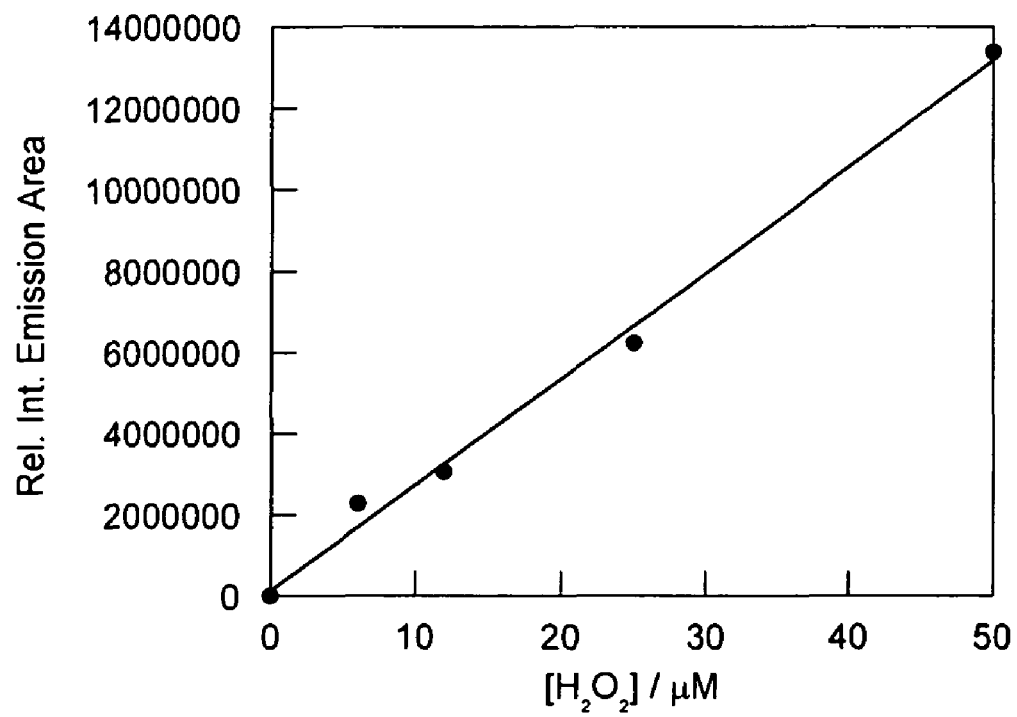
FIG. 12 is the fluorescence responses of 10 μM PX1 to various concentrations of $H_2O_2$. Spectra were acquired in 20 mM HEPES, pH 7, and all data were obtained after incubation with $H_2O_2$ at 25° C. for 15 min. Collected emission was integrated between 370 and 600 nm ($\lambda_{exc}$=350 nm).

The fluorescence responses of the Peroxysensor reagents were characterized over a wide range of $H_2O_2$ concentrations. FIG. 10, FIG. 11 and FIG. 12 display calibration plots for PF1, PR1, and PX1, respectively, showing a linear correlation between $H_2O_2$ concentrations and observed fluorescence responses in the range of 0 to 50 µM $H_2O_2$ with 5-10 µM dye. Under these conditions, all three probes can reliably detect down to 100-200 nM $H_2O_2$ in aqueous solution.

Example 3

3.1 Fluorescence Detection of $H_2O_2$ in Living Cells Using Confocal- and Two-Photon Microscopy The family of red-, green-, and blue-fluorescent reagents for the optical detection of $H_2O_2$ in living biological samples. Initial imaging studies demonstrate the ability of PF1 to respond to changes in $H_2O_2$ concentrations within living mammalian cells in culture. Incubation of HEK cells with 5 µM PF1 for 5 min at 25° C. results in negligible intracellular background fluorescence from the uncaged dye, as determined from scanning confocal microscopy measurements on live samples with one-photon excitation at 488 nm (FIG. 13a). Upon addition of physiologically relevant concentrations of $H_2O_2$ to the PF1-loaded cells (10-100 µM, FIG. 13b), prompt increases in intracellular green fluorescence are observed. Control experiments performed without dye or $H_2O_2$ give no fluorescence responses over background. In addition, brightfield transmission measurements (not shown) after PF1 incubation and $H_2O_2$ treatment confirm that the cells are viable throughout the imaging experiments. The foregoing experiments establish that PF1 can passively enter live cells and monitor changes in intracellular $H_2O_2$ concentrations.

An analogous set of experiments reveals that PR1 provides a useful red-fluorescent complement to PF1 for imaging $H_2O_2$ in biological samples. Live HEK cells incubated with 10 µM PR1 for 10 min at 25° C. show virtually no background fluorescence from the boronate-protected probe upon scanning with one-photon excitation at 543 nm (FIG. 14a). Striking increases in intracellular red fluorescence are observed upon treatment of the PR1-loaded cells with 100 µM $H_2O_2$ (FIG. 14b). Control experiments with cells excluding probe or $H_2O_2$ addition give negligible fluorescence responses, and the cells are viable throughout the experiments. The results show that PR1 is membrane-permeable and can respond to changes in intracellular $H_2O_2$ concentrations.

Alternative methods were explored for applying the blue-fluorescent PX1 reporter toward intracellular $H_2O_2$ detection, reasoning that its short ultraviolet excitation maximum (~350 nm) would promote interfering absorbance, scattering, and background autofluorescence from native cellular species. In this regard, two-photon microscopy is a technique that has facilitated the investigation of living systems with fluorescent reporters. Whereas one-photon fluorescence microscopy uses a single photon to excite a fluorophore into its excited state, two-photon fluorescence microscopy uses two photons of lower energy light to generate a fluorophore excited state. Advantages of two-photon excitation include reduced photodamage to living biological samples and fluorophore, minimized background absorption and scattering, improved spatial resolution and sensitivity, and the ability to image thicker specimens. We performed a series of experiments to evaluate the utility of PX1 for intracellular $H_2O_2$ imaging using two-photon microscopy. Incubation of live HEK cells with 10 µM PX1 for 2-3 min at 25° C. gave minimal intracellular background fluorescence as determined from scanning two-photon microscopy measurements with 704-nm excitation (FIG. 15a). Control cells without probe give the same fluorescence response, establishing that the observed background signal is from endogenous cellular species. Prompt increases in intracellular blue fluorescence are observed upon the addition of 100 µM concentrations of exogenous $H_2O_2$ to the PX1-stained cells (FIG. 15b). Control experiments carried out without fluorophore or $H_2O_2$ do not show any fluorescence enhancements. These data establish that PX1 undergoes effective two-photon excitation and is capable of imaging changes in intracellular $H_2O_2$ concentrations within living cells using two-photon microscopy.

Finally, the successful use of the Peroxysensor probes for monitoring changes in intracellular $H_2O_2$ concentrations in mammalian cell lines using either confocal or two-photon microscopy led us to evaluate their utility in primary culture systems. Cultured embryonic rat hippocampal neurons (E18) were incubated with 10 µM PF1 for 5 min at 25° C. and show negligible background fluorescence due to the unreacted probe. Placing these PF1-loaded neurons under simulated conditions of oxidative stress (300 µM $H_2O_2$ for 30 min at 25° C.) triggers notable increases in intracellular fluorescence. Control neurons without PF1 and/or $H_2O_2$ treatment show no detectable fluorescence enhancements. These experiments confirm that PF1 can be used in living neurons to detect oxidative stress events.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications are incorporated herein by reference.

The invention claimed is:

1. A pro-fluorescent compound having the formula:

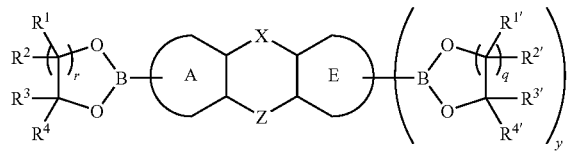

wherein

A and E are members independently selected from substituted or unsubstituted aryl wherein said substituted aryl is substituted with a group selected from halogen, R', =O, —OR', =NR', —NR'R", —NR"C(O)R', —CONR'R", —CO$_2$R' and —OC(O)R', wherein R' and R" are independently selected from H and (C$_1$-C$_8$) alkyl;

X is O;

Z is a member selected from CR$^5$, C(O), NR$^5$ and substituted or unsubstituted heterocycloalkyl wherein R$^5$ is a member selected from H, unsubstituted alkyl, and substituted or unsubstituted aryl, wherein said substituted aryl is substituted with a group selected from halogen, R', =O, —OR', =NR', —NR'R", —NR"C(O)R', —CONR'R", —CO$_2$R', —OC(O)R', and a linker covalently attached to a member selected from a reactive functional group and a carrier selected from the group consisting of synthetic polymers and biomolecules, wherein R' and R" are independently selected from H and (C$_1$-C$_8$) alkyl; and said substituted heterocycloalkyl is substituted with a group selected from halogen, =O, —OR', =NR', —NR'R", —NR"C(O)R', —CONR'R", —CO$_2$R', —OC(O)R', and a linker covalently attached to a member selected from a reactive functional group and a carrier selected from the group consisting of synthetic polymers and biomolecules, wherein R' and R" are independently selected from H and unsubstituted alkyl;

y is an integer selected from 0 and 1;

q and r are members independently selected from 1, 2 and 3; and $R^1$, $R^{1'}$, $R^2$, $R^{2'}$, $R^3$, $R^{3'}$, $R^4$ and $R^{4'}$ are members independently selected from H, unsubstituted alkyl, and unsubstituted heteroalkyl.

2. The compound according to claim 1, having the formula:

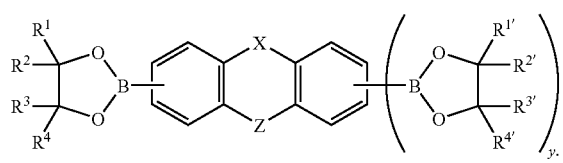

3. The compound according to claim 2, having the formula:

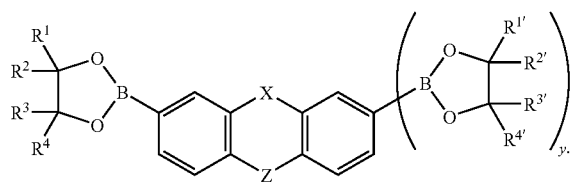

4. The compound according to claim 1, having the formula:

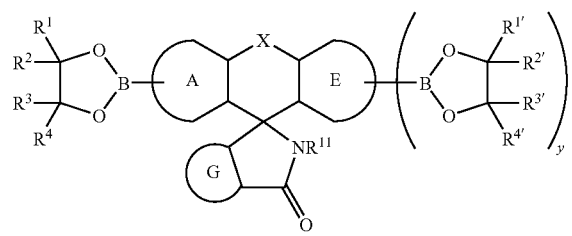

wherein
$R^{11}$ is a linker covalently attached to a member selected from a reactive functional group and a carrier selected from the group consisting of synthetic polymers and biomolecules; and G is a member selected from substituted or unsubstituted aryl.

5. The compound according to claim 1, wherein said compound is covalently attached to a carrier species selected from the group consisting of synthetic polymers and biomolecules.

6. The compound according to claim 5, wherein said biomolecule is a member selected from the group consisting of antibodies, antigens, peptides, nucleic acids, enzymes, haptens, carbohydrates and pharmacologically active agents.

7. A method for assaying a sample for a selected analyte, said method comprising:
(a) contacting said sample with a pro-fluorescent compound according to claim 1, under conditions appropriate to convert said compound to a fluorescent compound;

(b) exciting said fluorescent compound; and
(c) determining a fluorescence property of said sample, wherein the presence of said analyte in said sample results in a change in said fluorescence property.

8. The method according to claim 7, wherein said analyte converts said pro-fluorescent compound into said fluorescent compound.

9. A method for determining whether a compound alters an activity of an enzyme, said method comprising:
(a) contacting a sample comprising said enzyme with a profluorescent compound according to claim 1 under conditions appropriate for said enzyme to convert said pro-fluorescent compound into a fluorescent compound;
(b) exciting said compound; and
(c) determining a fluorescence property of said sample, wherein said activity of said enzyme in said sample results in a change in said fluorescence property.

10. The method according to claim 9, wherein said enzyme generates a product that converts said profluorescent compound into said fluorescent compound.

11. A microarray comprising a compound according to claim 1, said compound being conjugated directly to a solid support, conjugated through a linker, or conjugated to a carrier species attached to said solid support.

12. The microarray according to claim 11, wherein said carrier species is a member selected from a biomolecule, a synthetic polymer and combinations thereof.

13. The microarray according to claim 11, wherein said solid support is divided into a first region and a second region, said first region having attached thereto a first said compound and said second region having attached thereto a second said compound.

14. A compound having a formula selected from:

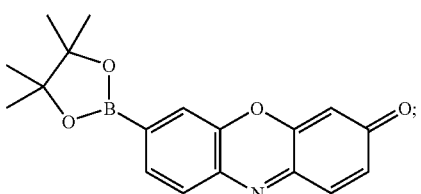

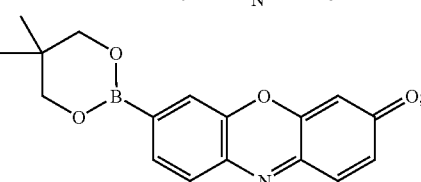

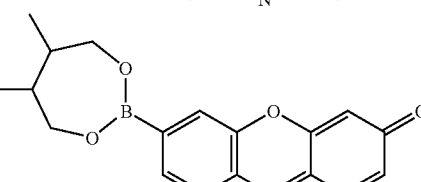

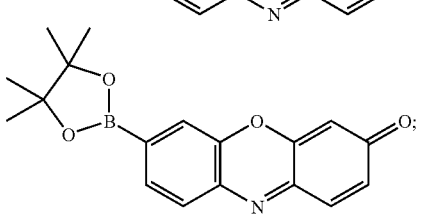

-continued
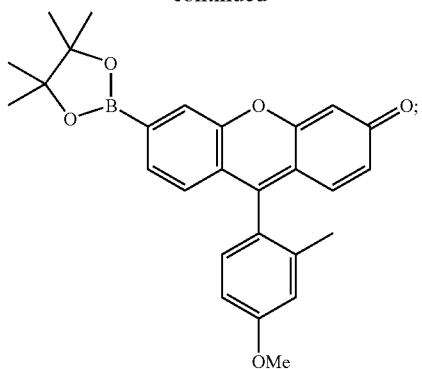
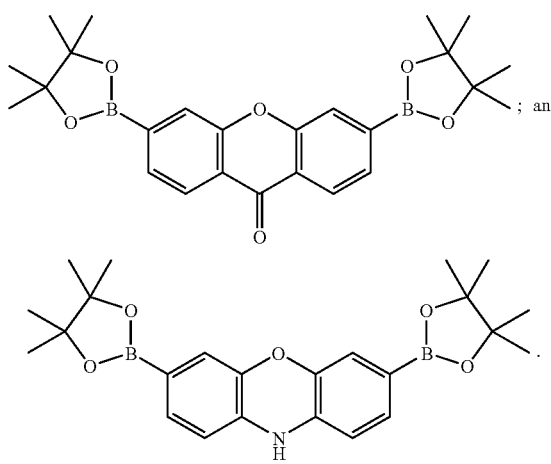
15. A compound having the formula:
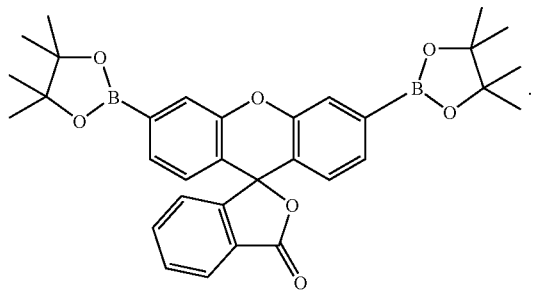
16. The compound of claim 1 having the formula:
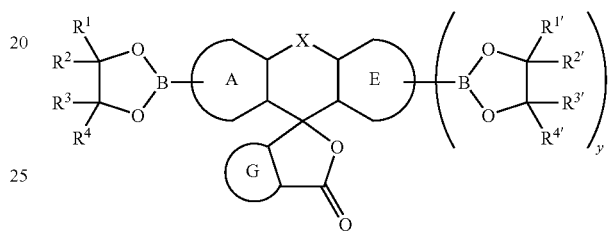
wherein G is a substituted or unsubstituted phenyl ring fused to the heterocycle.
17. The compound of claim 1 wherein Z is selected from C(O), $NR^5$ and substituted or unsubstituted heterocycloalkyl.
18. The compound of claim 1 wherein Z is selected from C(O) and $NR^5$.
* * * * *